United States Patent
Yasunaga

(10) Patent No.: US 7,125,715 B2
(45) Date of Patent: Oct. 24, 2006

(54) NUCLEIC ACID ENCODING A POLYPEPTIDE PROMOTING TYPE II COLLAGEN FORMATION AND AGGRECAN PRODUCTION

(75) Inventor: Kunio Yasunaga, Ibaraki (JP)

(73) Assignee: Astellas Pharma Inc.(JP)

( * ) Notice: Subject to any disclaimer, the term of this patent is extended or adjusted under 35 U.S.C. 154(b) by 413 days.

(21) Appl. No.: 10/240,535

(22) PCT Filed: Nov. 21, 2001

(86) PCT No.: PCT/JP01/10150

§ 371 (c)(1), (2), (4) Date: Oct. 2, 2002

(87) PCT Pub. No.: WO02/42448

PCT Pub. Date: May 30, 2002

(65) Prior Publication Data

US 2003/0153732 A1 Aug. 14, 2003

(30) Foreign Application Priority Data

Nov. 22, 2000 (JP) ............................ 2000-356378

(51) Int. Cl.
- *C12N 5/00* (2006.01)
- *C12N 1/20* (2006.01)
- *C12N 1/14* (2006.01)
- *C12N 15/00* (2006.01)
- *C07H 21/04* (2006.01)
- *C12N 9/64* (2006.01)

(52) U.S. Cl. .................. 435/325; 435/410; 435/252.3; 435/254.11; 435/320.1; 435/226; 536/23.2; 536/23.5

(58) Field of Classification Search ............... 530/350; 536/23.5; 435/320.1, 325, 419, 252.3, 254.11; 514/44

See application file for complete search history.

(56) References Cited

U.S. PATENT DOCUMENTS 6,586,390 B1 * 7/2003 Haley et al. .................. 514/2

FOREIGN PATENT DOCUMENTS

| WO | WO 96/38168 A1 | 12/1996 |
|---|---|---|
| WO | WO 98/51317 A1 | 11/1998 |
| WO | WO 01/05825 A2 | 1/2001 |
| WO | WO 01/05825 A3 | 1/2001 |
| WO | WO 01/53456 A2 | 7/2001 |
| WO | WO 01/53456 A3 | 7/2001 |
| WO | WO 01/55437 A2 | 8/2001 |

OTHER PUBLICATIONS

Harrison et al. (1991) Exp Cell Res 192:340-345.*
Adolphe et al. (1984) Exp Cell Res 155:527-536.*
Branden et al. "Introduction to Protein Structure", Garland Publishing Inc., New York, 1991, p. 247.*
Witkowski et al. (1999) Biochemistry 38:11643-11650.*
Dang et al. (1999) Clin Can Res 5:471-474.*
Fox (2003) Nat Biotechnol 21:217.*
Wozney et al. (1988) Science 242:1528-1534.*
Sailor et al. (1996) J Orthop Res 14:937-945; abstract only.*
European Search Report mailed Dec. 3. 2004, for European Patent Application No. 01997548.1, which is a national phase filing of PCT Application No. PCT/JP01/10150, filed Nov. 21, 2001.
Davis et al., Dec. 27, 1996, "Isolation of Angiopoietin-1, a Ligand for the TIE2 Receptor, by Secretion-Trap Expression Cloning," Cell, 87(7): 1161-1169.
Gerber et al., Jun. 1999, "VEGF couples hypertrophic cartilage remodeling, ossification and angiogenesis during endochondral bone formation," Nature Medicine, 5(6): 623-628.
Haigh et al., Mar. 7, 2000, "Conditional inactivation of VEGF-A in areas of collagen2a1 expression results in embryonic lethality in the heterozygous state," Development, 127: 1445-1453.
Hänsch et al., Jun. 1995, "Matrix Protein Synthesis by Glomerular Mesangial Cells in Culture: Effects of Transforming Growth Factor β (TGFβ) and Platelet-Derived Growth Factor (PDGF) on Fibronectin and Collagen Type IV mRNA," J. Cellular Physiology, 163(3):451-457.
Satoh et al., May 15, 1998, "Functional Analysis of Diastrophic Dysplasia Sulfate Transporter," J. Biological Chemistry, 273(20): 12307-12315.

* cited by examiner

Primary Examiner—David J. Steadman
(74) Attorney, Agent, or Firm—Finnegan, Henderson, Farabow, Garrett & Dunner LLP

(57) ABSTRACT

A novel polypeptide, a polynucleotide encoding this polypeptide, an expression vector comprising this polynucleotide, a cell transfected with the expression vector, and a pharmaceutical composition for promoting type II collagen production, a pharmaceutical composition for promoting aggrecan production, and a pharmaceutical composition for treating and/or preventing osteoarthritis comprising the above polypeptide as an active ingredient are disclosed. The polypeptide exhibits an activity of promoting type II collagen production and/or an activity of promoting aggrecan production.

3 Claims, 1 Drawing Sheet

SEQUENCE LISTING

```
<160> NUMBER OF SEQ ID NOS: 36

<210> SEQ ID NO 1
<211> LENGTH: 1702
<212> TYPE: DNA
<213> ORGANISM: Homo sapiens
<220> FEATURE:
<221> NAME/KEY: CDS
<222> LOCATION: (37)..(1203)

<400> SEQUENCE: 1
tatttgaaga agtgttttca tctatccaag aaaaat atg atg tct cca tcc caa         54
                                        Met Met Ser Pro Ser Gln
                                          1               5 gcc tca ctc tta ttc tta aat gta tgt att ttt att tgt gga gaa gct        102
Ala Ser Leu Leu Phe Leu Asn Val Cys Ile Phe Ile Cys Gly Glu Ala
             10                  15                  20 gta caa ggt aac tgt gta cat cat tct acg gac tct tca gta gtt aac        150
Val Gln Gly Asn Cys Val His His Ser Thr Asp Ser Ser Val Val Asn
         25                  30                  35 att gta gaa gat gga tct aat gca aaa gat gaa agt aaa agt aat gat        198
Ile Val Glu Asp Gly Ser Asn Ala Lys Asp Glu Ser Lys Ser Asn Asp
     40                  45                  50 act gtt tgt aag gaa gac tgt gag gaa tca tgt gat gtt aaa act aaa        246
Thr Val Cys Lys Glu Asp Cys Glu Glu Ser Cys Asp Val Lys Thr Lys
 55                  60                  65                  70 att aca cga gaa gaa aaa cat ttc atg tgt aga aat ttg caa aat tct        294
Ile Thr Arg Glu Glu Lys His Phe Met Cys Arg Asn Leu Gln Asn Ser
                 75                  80                  85 att gtt tcc tac aca aga agt acc aaa aaa cta cta agg aat atg atg        342
Ile Val Ser Tyr Thr Arg Ser Thr Lys Lys Leu Leu Arg Asn Met Met
             90                  95                 100 gat gag caa caa gct tcc ttg gat tat tta tct aat cag gtt aac gag        390
Asp Glu Gln Gln Ala Ser Leu Asp Tyr Leu Ser Asn Gln Val Asn Glu
```

```
                    105                 110                 115
ctc atg aat aga gtt ctc ctt ttg act aca gaa gtt ttt aga aaa cag    438
Leu Met Asn Arg Val Leu Leu Leu Thr Thr Glu Val Phe Arg Lys Gln
    120                 125                 130 ctg gat cct ttt cct cac aga cct gtt cag tca cat ggt tta gat tgc    486
Leu Asp Pro Phe Pro His Arg Pro Val Gln Ser His Gly Leu Asp Cys
135                 140                 145                 150 act gat att aag gat acc att ggc tct gtc acc aaa aca ccg agt ggt    534
Thr Asp Ile Lys Asp Thr Ile Gly Ser Val Thr Lys Thr Pro Ser Gly
                155                 160                 165 tta tac ata att cac cca gaa gga tct agc tac cca ttt gag gta atg    582
Leu Tyr Ile Ile His Pro Glu Gly Ser Ser Tyr Pro Phe Glu Val Met
            170                 175                 180 tgt gac atg gat tac aga gga ggt gga cgg act gtg ata cag aaa aga    630
Cys Asp Met Asp Tyr Arg Gly Gly Gly Arg Thr Val Ile Gln Lys Arg
        185                 190                 195 att gat ggg ata att gat ttc cag agg ttg tgg tgt gat tat ctg gat    678
Ile Asp Gly Ile Ile Asp Phe Gln Arg Leu Trp Cys Asp Tyr Leu Asp
    200                 205                 210 gga ttt gga gat ctt cta gga gaa ttt tgg cta gga ctg aaa aag att    726
Gly Phe Gly Asp Leu Leu Gly Glu Phe Trp Leu Gly Leu Lys Lys Ile
215                 220                 225                 230 ttt tat ata gta aat cag aaa aat acc agt ttt atg ctg tat gtg gct    774
Phe Tyr Ile Val Asn Gln Lys Asn Thr Ser Phe Met Leu Tyr Val Ala
                235                 240                 245 ttg gaa tct gaa gat gac act ctt gct tat gca tca tat gat aat ttt    822
Leu Glu Ser Glu Asp Asp Thr Leu Ala Tyr Ala Ser Tyr Asp Asn Phe
            250                 255                 260 tgg cta gag gat gaa acg aga ttt ttt aaa atg cac tta gga cgg tat    870
Trp Leu Glu Asp Glu Thr Arg Phe Phe Lys Met His Leu Gly Arg Tyr
        265                 270                 275 tca gga aat gct ggt gat gca ttc cgg ggt ctc aaa aaa gaa gat aat    918
Ser Gly Asn Ala Gly Asp Ala Phe Arg Gly Leu Lys Lys Glu Asp Asn
    280                 285                 290 caa aat gca atg cct ttt agc aca tca gat gtt gat aat gat ggg tgt    966
Gln Asn Ala Met Pro Phe Ser Thr Ser Asp Val Asp Asn Asp Gly Cys
295                 300                 305                 310 cgc cct gca tgc ctg gtc aat ggt cag tct gtg aag agc tgc agt cac   1014
Arg Pro Ala Cys Leu Val Asn Gly Gln Ser Val Lys Ser Cys Ser His
                315                 320                 325 ctc cat aac aag acc ggc tgg tgg ttt aac gag tgt ggt cta gca aat   1062
Leu His Asn Lys Thr Gly Trp Trp Phe Asn Glu Cys Gly Leu Ala Asn
            330                 335                 340 cta aat ggc att cat cac ttc tct gga aaa ttg ctt gca act gga att   1110
Leu Asn Gly Ile His His Phe Ser Gly Lys Leu Leu Ala Thr Gly Ile
        345                 350                 355 caa tgg ggc acg tgg acc aaa aac aac tca cct gtc aag att aaa tct   1158
Gln Trp Gly Thr Trp Thr Lys Asn Asn Ser Pro Val Lys Ile Lys Ser
    360                 365                 370 gtt tca atg aaa att aga aga atg tac aat cca tat ttt aaa taa       1203
Val Ser Met Lys Ile Arg Arg Met Tyr Asn Pro Tyr Phe Lys
375                 380                 385 tctcatttaa cattgtaatg caagttctac aatgataata tattaaagat ttttaaagt  1263 ttatcttttc acttagtgtt tcaaacatat taggcaaaat ttaactgtag atggcattta  1323
gatgttatga gtttaattag aaaacttcaa ttttgtagta ttctataaaa gaaaacatgg  1383
cttattgtat gttttacttt ctgactatat taacaatata caatgaaatt tgtttcaagt  1443
gaactacaac ttgtcttcct aaaatttata gtgattttaa aggattttgc cttttctttg  1503
```

-continued

```
aagcattttt aaaccataat atgttgtaag gaaaattgaa gggaatatttt tacttatttt     1563 tatactttat atgattatat aatctacaga taatttctac tgaagacagt tacaataaat     1623
aactttatgc agattaatat ataagctaca catgatgtaa aaaccttact atttctaggt     1683
gatgccatac cattttaaa                                                  1702
```

<210> SEQ ID NO 2
<211> LENGTH: 388
<212> TYPE: PRT
<213> ORGANISM: Homo sapiens

<400> SEQUENCE: 2

```
Met Met Ser Pro Ser Gln Ala Ser Leu Leu Phe Leu Asn Val Cys Ile
 1               5                  10                  15

Phe Ile Cys Gly Glu Ala Val Gln Gly Asn Cys Val His His Ser Thr
                20                  25                  30

Asp Ser Ser Val Val Asn Ile Val Glu Asp Gly Ser Asn Ala Lys Asp
            35                  40                  45

Glu Ser Lys Ser Asn Asp Thr Val Cys Lys Glu Asp Cys Glu Glu Ser
        50                  55                  60

Cys Asp Val Lys Thr Lys Ile Thr Arg Glu Glu Lys His Phe Met Cys
    65                  70                  75                  80

Arg Asn Leu Gln Asn Ser Ile Val Ser Tyr Thr Arg Ser Thr Lys Lys
                85                  90                  95

Leu Leu Arg Asn Met Met Asp Glu Gln Gln Ala Ser Leu Asp Tyr Leu
            100                 105                 110

Ser Asn Gln Val Asn Glu Leu Met Asn Arg Val Leu Leu Thr Thr
        115                 120                 125

Glu Val Phe Arg Lys Gln Leu Asp Pro Phe Pro His Arg Pro Val Gln
    130                 135                 140

Ser His Gly Leu Asp Cys Thr Asp Ile Lys Asp Thr Ile Gly Ser Val
145                 150                 155                 160

Thr Lys Thr Pro Ser Gly Leu Tyr Ile Ile His Pro Glu Gly Ser Ser
                165                 170                 175

Tyr Pro Phe Glu Val Met Cys Asp Met Asp Tyr Arg Gly Gly Gly Arg
            180                 185                 190

Thr Val Ile Gln Lys Arg Ile Asp Gly Ile Ile Asp Phe Gln Arg Leu
        195                 200                 205

Trp Cys Asp Tyr Leu Asp Gly Phe Gly Asp Leu Leu Gly Glu Phe Trp
    210                 215                 220

Leu Gly Leu Lys Lys Ile Phe Tyr Ile Val Asn Gln Lys Asn Thr Ser
225                 230                 235                 240

Phe Met Leu Tyr Val Ala Leu Glu Ser Glu Asp Asp Thr Leu Ala Tyr
                245                 250                 255

Ala Ser Tyr Asp Asn Phe Trp Leu Glu Asp Glu Thr Arg Phe Phe Lys
            260                 265                 270

Met His Leu Gly Arg Tyr Ser Gly Asn Ala Gly Asp Ala Phe Arg Gly
        275                 280                 285

Leu Lys Lys Glu Asp Asn Gln Asn Ala Met Pro Phe Ser Thr Ser Asp
    290                 295                 300

Val Asp Asn Asp Gly Cys Arg Pro Ala Cys Leu Val Asn Gly Gln Ser
305                 310                 315                 320

Val Lys Ser Cys Ser His Leu His Asn Lys Thr Gly Trp Trp Phe Asn
```

-continued

```
                        325                 330                 335
    Glu Cys Gly Leu Ala Asn Leu Asn Gly Ile His His Phe Ser Gly Lys
                340                 345                 350
    Leu Leu Ala Thr Gly Ile Gln Trp Gly Thr Trp Thr Lys Asn Asn Ser
            355                 360                 365
    Pro Val Lys Ile Lys Ser Val Ser Met Lys Ile Arg Arg Met Tyr Asn
        370                 375                 380
    Pro Tyr Phe Lys
    385

<210> SEQ ID NO 3
<211> LENGTH: 28
<212> TYPE: DNA
<213> ORGANISM: Homo sapiens

<400> SEQUENCE: 3
gggcgacacc catcattatc aacatctg                                    28

<210> SEQ ID NO 4
<211> LENGTH: 28
<212> TYPE: DNA
<213> ORGANISM: Homo sapiens

<400> SEQUENCE: 4
cttttctgta tcacagtccg tccacctc                                    28

<210> SEQ ID NO 5
<211> LENGTH: 27
<212> TYPE: DNA
<213> ORGANISM: Homo sapiens

<400> SEQUENCE: 5
tcagatgttg ataatgatgg gtgtcgc                                     27

<210> SEQ ID NO 6
<211> LENGTH: 26
<212> TYPE: DNA
<213> ORGANISM: Homo sapiens

<400> SEQUENCE: 6
ctgcagtcac ctccataaca agaccg                                      26

<210> SEQ ID NO 7
<211> LENGTH: 21
<212> TYPE: DNA
<213> ORGANISM: Homo sapiens

<400> SEQUENCE: 7
aagtgttttc atctatccaa g                                           21

<210> SEQ ID NO 8
<211> LENGTH: 28
<212> TYPE: DNA
<213> ORGANISM: Homo sapiens

<400> SEQUENCE: 8
ggacggactg tgatacagaa aagaattg                                    28

<210> SEQ ID NO 9
<211> LENGTH: 33
<212> TYPE: DNA
<213> ORGANISM: Artificial Sequence
```

```
<220> FEATURE:
<223> OTHER INFORMATION: Description of Artificial Sequence: an
      artificially synthesized primer sequence

<400> SEQUENCE: 9
ttgcggccgc tttaaaatat ggattgtaca ttc                              33

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 10
ctagcgcggc cgcaggatcc gactacaagg acgacgatga caaatgataa             50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 11
gatcttatca tttgtcatcg tcgtccttgt agtcggatcc tgcggccgcg             50

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 12
ggactagtct agaagctggg taccagctgc tagc                              34

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 13
ggactagtgt cgaccggtca tggctgcgc                                   29

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 14
caggtaccac catgatgtct ccatcccaag cctc                              34

<210> SEQ ID NO 15
<211> LENGTH: 40
<212> TYPE: DNA
<213> ORGANISM: Artificial Sequence
<220> FEATURE:
```

<223> OTHER INFORMATION: Description of Artificial Sequence: an
      artificially synthesized primer sequence

<400> SEQUENCE: 15
tctctagact gatcaccatg atgtctccat cccaagcctc                    40

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 16
cgtctagatt atcatttgtc atcgtcgt                                 28

<210> SEQ ID NO 17
<211> LENGTH: 97
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 17
agcttgccac catgaagacg atcatcgccc tgagctacat cttctgcctg gtattcgccg    60
actacaagga cgatgatgac aagggatcc actagtc                             97

<210> SEQ ID NO 18
<211> LENGTH: 97
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 18
tcgagactag tggatcccct tgtcatcatc gtccttgtag tcggcgaata ccaggcagaa    60
gatgtagctc agggcgatga tcgtcttcat ggtggca                            97

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 19
cctgatcact gtacaaggta actgtgtaca t                             31

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 20
gtctcgagtt atttaaaata tggattgt                                 28

<210> SEQ ID NO 21
<211> LENGTH: 29

```
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 21
agtctagagc caccatgaag acgatcatc                                    29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 22
catctagatt atttaaaata tggattgta                                    29

<210> SEQ ID NO 23
<211> LENGTH: 27
<212> TYPE: DNA
<213> ORGANISM: Homo sapiens

<400> SEQUENCE: 23
cattgaaaca gatttaatct tgacagg                                      27

<210> SEQ ID NO 24
<211> LENGTH: 22
<212> TYPE: DNA
<213> ORGANISM: Homo sapiens

<400> SEQUENCE: 24
caacgaattt ggctacagca ac                                           22

<210> SEQ ID NO 25
<211> LENGTH: 22
<212> TYPE: DNA
<213> ORGANISM: Homo sapiens

<400> SEQUENCE: 25
ctacatggca actgtgagga gg                                           22

<210> SEQ ID NO 26
<211> LENGTH: 20
<212> TYPE: DNA
<213> ORGANISM: Homo sapiens

<400> SEQUENCE: 26
tttcccaggt caagatggtc                                              20

<210> SEQ ID NO 27
<211> LENGTH: 20
<212> TYPE: DNA
<213> ORGANISM: Homo sapiens

<400> SEQUENCE: 27
cttcagcacc tgtctcacca                                              20

<210> SEQ ID NO 28
<211> LENGTH: 20
<212> TYPE: DNA
<213> ORGANISM: Homo sapiens
```

```
<400> SEQUENCE: 28
gtgttgctgg tgaaaagggt                                           20

<210> SEQ ID NO 29
<211> LENGTH: 20
<212> TYPE: DNA
<213> ORGANISM: Homo sapiens

<400> SEQUENCE: 29
gggatcccac tggtcctaat                                           20

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 30
aggtaccacc atgatgtctc catcccaagc ctc                            33

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 31
ttctcgagtt atcatttgtc atcgtcgt                                  28

<210> SEQ ID NO 32
<211> LENGTH: 22
<212> TYPE: DNA
<213> ORGANISM: Homo sapiens

<400> SEQUENCE: 32
aaggctccca gaacatcacc ta                                        22

<210> SEQ ID NO 33
<211> LENGTH: 23
<212> TYPE: DNA
<213> ORGANISM: Homo sapiens

<400> SEQUENCE: 33
ccggtactcg ataacagtct tgc                                       23

<210> SEQ ID NO 34
<211> LENGTH: 21
<212> TYPE: DNA
<213> ORGANISM: Homo sapiens

<400> SEQUENCE: 34
tatggcatcc gagacaccaa c                                         21

<210> SEQ ID NO 35
<211> LENGTH: 23
<212> TYPE: DNA
<213> ORGANISM: Homo sapiens

<400> SEQUENCE: 35
ctggaaggtg aacttctctg gag                                       23
```

-continued

```
<210> SEQ ID NO 36
<211> LENGTH: 30
<212> TYPE: DNA
<213> ORGANISM: Homo sapiens

<400> SEQUENCE: 36
agacctatga tgtgtactgc ttcgccgagg                                        30
```

NUCLEIC ACID ENCODING A POLYPEPTIDE PROMOTING TYPE II COLLAGEN FORMATION AND AGGRECAN PRODUCTION

TECHNICAL FIELD

The present invention relates to a novel polypeptide.

BACKGROUND ART

Osteoarthritis (hereinafter sometimes referred to as "OA") is the most common disease among patients with joint diseases in which major lesions are damage to and/or degeneration of articular cartilage. Among the present medication for the OA disease, an analgesic and antiinflammatory agent or a hyaluronic acid preparation is used as a symptomatic treatment to alleviate pain, but satisfactory effects are not achieved, and thus the patient finally reaches a condition in which surgical treatment is necessary.

It is considered that articular cartilage is a tissue deficient in ability for regeneration. As examples of the development of a therapy for restoring articular cartilage in the OA disease, a method for removing articular chondrocytes from a body, culturing the cells in vitro, and implanting the proliferated cells in the damaged articular site is known. However, this method requires a surgical operation and has many problems, and thus is not established as a useful therapy (Onstott A. T. et al., AORN J., 71, 843–845, 848–851, 2000). Further, an attempt to use several physiologically active substances exhibiting a differentiation inducing activity for chondrocytes as a therapeutic agent is carried out. However, the effect of this is now being evaluated in an animal model in which articular cartilage is artificially damaged, and the attempt has not reached the stage of clinical application (Sellers R. S. et al., J. Bone Joint Surg. Am., 79A, 1452–1463, 1997; and Trippel S. B., J. Rheumatol. Suppl., 43, 129–132, 1995).

Blood vessels, nerves, and lymph ducts do not exist in a cartilage tissue. Articular cartilage is composed of chondrocytes, and an extracellular matrix produced by the chondrocytes. The extracellular matrix such as type II collagen or proteoglycan produced by articular chondrocytes gives a specific elasticity and strength and a resistance against pressure to the cartilage tissue, and then plays an important role in functioning as articular cartilage (Huber M. et al., Investigative Radiology, 35(10), 573–580, 2000). However, in the OA disease, degeneration of the articular cartilage tissue or fibrocartilage formation occurs. In particular, type II collagen is decomposed, and thus the amount of type II collagen, which normally functions significantly, decreases [Hollander A. P. et al., J. Clin. Invest., 93(4), 1722–1732, 1994].

Similarly to type II collagen, aggrecan is produced by articular chondrocytes and a major proteoglycan forming the cartilaginous tissue. Aggrecan plays an important role in carrying out a function as articular cartilage, but a decomposition and degeneration of aggrecan are observed in the OA disease [Neame P. J. et al., J. Fla. Med. Assoc., 81(3), 191–193, 1994].

DISCLOSURE OF INVENTION

The object of the present invention is to provide a substance having an activity of promoting type II collagen production and/or an activity of promoting aggrecan production, which is useful for treating OA, and a novel pharmaceutical composition for treating and/or preventing OA.

With the aim of solving the aforementioned problems, the present inventors have conducted intensive studies and, as a result, found a novel polynucleotide encoding a novel polypeptide exhibiting an activity of promoting type II collagen production. Next, the inventors confirmed that the polynucleotide is specifically expressed in an articular cartilage, by analyzing a distribution of the mRNA expression of the polynucleotide. Further, the inventors confirmed that the polynucleotide is located on 11q22 of human chromosomes. It is known that Osteoarthritis-susceptibility is linked on this locus. Furthermore, by overexpressing the polypeptide in human chondrocyte, the inventors confirmed that the polypeptide promotes type II collagen production and aggrecan production and is useful for treating and/or preventing OA, and completed the present invention.

The present invention relates to:

[1] (1) a polypeptide having an amino acid sequence consisting of the 23rd to 388th amino acids in an amino acid sequence of SEQ ID NO: 2, or (2) a polypeptide having an amino acid sequence in which one or plural amino acids are deleted, substituted, and/or added at one or plural positions in an amino acid sequence consisting of the 23rd to 388th amino acids in an amino acid sequence of SEQ ID NO: 2, and exhibiting an activity of promoting type II collagen production and/or an activity of promoting aggrecan production;

[2] a polypeptide comprising an amino acid sequence consisting of the 23rd to 388th amino acids in an amino acid sequence of SEQ ID NO: 2, and exhibiting an activity of promoting type II collagen production and/or an activity of promoting aggrecan production;

[3] a polypeptide having an amino acid sequence having a 90% or more homology with an amino acid sequence consisting of the 23rd to 388th amino acids in an amino acid sequence of SEQ ID NO: 2 or with an amino acid sequence of SEQ ID NO: 2, and exhibiting an activity of promoting type II collagen production and/or an activity of promoting aggrecan production;

[4] the polypeptide of the items [1] to [3], exhibiting an activity of promoting type II collagen production and an activity of promoting aggrecan production;

[5] a polypeptide having an amino acid sequence consisting of the 1st to 388th or 23rd to 388th amino acids in an amino acid sequence of SEQ ID NO: 2;

[6] a polynucleotide encoding the polypeptide of the items [1] to [5];

[7] an expression vector comprising the polynucleotide of the item [6];

[8] a cell transfected with the expression vector of the item [7];

[9] a pharmaceutical composition for promoting type II collagen production, comprising the polypeptide of the items [1] to [5], the polynucleotide of the item [6], or the expression vector of the item [7], and a pharmaceutically acceptable carrier;

[10] a pharmaceutical composition for promoting aggrecan production, comprising the polypeptide of the items [1] to [5], the polynucleotide of the item [6], or the expression vector of the item [7], and a pharmaceutically acceptable carrier;

[11] a pharmaceutical composition for treating and/or preventing osteoarthritis, comprising the polypeptide of the items [1] to [5], the polynucleotide of the item [6], or the expression vector of the item [7], and a pharmaceutically acceptable carrier;

[12] a method for promoting type II collagen production, comprising administering to a subject in need thereof the polypeptide of the items [1] to [5], the polynucleotide of the item [6], or the expression vector of the item [7] in an amount of effective thereof;

[13] a method for promoting aggrecan production, comprising administering to a subject in need thereof the polypeptide of the items [1] to [5], the polynucleotide of the item [6], or the expression vector of the item [7] in an amount of effective thereof;

[14] a method for treating and/or preventing osteoarthritis, comprising administering to a subject in need thereof the polypeptide of the items [1] to [5], the polynucleotide of the item [6], or the expression vector of the item [7] in an amount of effective thereof;

[15] use of the polypeptide of the items [1] to [5], the polynucleotide of the item [6], or the expression vector of the item [7], in the manufacture of a pharmaceutical composition for promoting type II collagen production, a pharmaceutical composition for promoting aggrecan production, or a pharmaceutical composition for treating and/or preventing osteoarthritis; and

[16] an antibody or a fragment thereof, which binds to the polypeptide of the items [1] to [5].

BEST MODE FOR CARRYING OUT THE INVENTION

Figure 1:
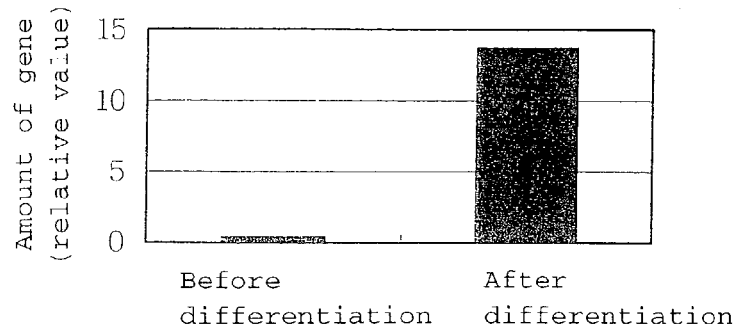
FIG. 1 is a graph showing the expression of the gene encoding the polypeptide of the present invention consisting of the amino acid sequence of SEQ ID NO: 2 before or after a differentiation to the chondrogenic lineage of human mesenchymal stem cells.

The present invention will be explained in detail hereinafter.

The polypeptide of the present invention includes (1) a polypeptide having an amino acid sequence consisting of the 23rd to 388th amino acids in the amino acid sequence of SEQ ID NO: 2 (hereinafter referred to as "polypeptide 23/388");

(2) a polypeptide having an amino acid sequence in which one or plural amino acids are deleted, substituted, and/or added at one or plural positions in the amino acid sequence (i.e., the amino acid sequence of the polypeptide 23/388) consisting of the 23rd to 388th amino acids in the amino acid sequence of SEQ ID NO: 2, and exhibiting an activity of promoting type II collagen production (preferably an activity of promoting type II collagen production in articular chondrocytes) and/or an activity of promoting aggrecan production (preferably an activity of promoting aggrecan production in articular chondrocytes) (hereinafter referred to as a variation functionally equivalent); and (3) a polypeptide having an amino acid sequence having a 90% or more homology with the amino acid sequence of the polypeptide 23/388 or with the amino acid sequence of SEQ ID NO: 2, and exhibiting an activity of promoting type II collagen production (preferably an activity of promoting type II collagen production in articular chondrocytes) and/or an activity of promoting aggrecan production (preferably an activity of promoting aggrecan production in articular chondrocytes) (hereinafter referred to as a homologous polypeptide).

Among the polypeptides (1) to (3) as the polypeptide of the present invention, a polypeptide exhibiting both the activity of promoting type II collagen production (preferably the activity of promoting type II collagen production in articular chondrocytes) and the activity of promoting aggrecan production (preferably the activity of promoting aggrecan production in articular chondrocytes) is preferable.

One of the polypeptides of the present invention, a polypeptide in which a secretory signal sequence is cleaved (it is presumed that the N-terminus is the 23rd amino acid in the amino acid sequence of SEQ ID NO: 2 and that it is the polypeptide 23/388), exhibits both the activity of promoting type II collagen production (preferably the activity of promoting type II collagen production in articular chondrocytes) and the activity of promoting aggrecan production (preferably the activity of promoting aggrecan production in articular chondrocytes).

A method for confirming whether or not a polypeptide to be tested exhibits the "activity of promoting type II collagen production (particularly the activity of promoting type II collagen production in articular chondrocytes)" as used herein is not particularly limited, but it can be confirmed by, for example, the following methods (preferably a method described in Example 12 or 16). In this method, desired cells (particularly human articular chondrocytes) are respectively transfected with an expression vector comprising a polynucleotide encoding the polypeptide or a control expression vector not comprising the polynucleotide. After a predetermined number of days, such as 3 days, from the transfection, an amount of type II collagen mRNA expressed in each cell is measured. When the amount of type II collagen mRNA expressed increases in the cells transfected with the expression vector comprising a polynucleotide encoding the polypeptide, in comparison with that transfected with the control expression vector, it can be decided that the polypeptide exhibits the "activity of promoting type II collagen production (particularly the activity of promoting type II collagen production in articular chondrocytes)".

Alternatively, appropriate cells (particularly human articular chondrocytes) are respectively infected with a virus obtained by transfection with a virus vector comprising a polynucleotide encoding the polypeptide or a control virus obtained by transfection with a control virus vector not comprising the polynucleotide. After a predetermined number of days, such as 4 or 7 days, from the infection, an amount of type II collagen mRNA expressed in each cell is measured. When the amount of type II collagen mRNA expressed increases in the cells infected with the virus obtained by transfection with a virus vector comprising a polynucleotide encoding the polypeptide, in comparison with that infected with the control virus, it can be decided that the polypeptide exhibits the "activity of promoting type II collagen production (particularly the activity of promoting type II collagen production in articular chondrocytes)".

A method for confirming whether or not a polypeptide to be tested exhibits the "activity of promoting aggrecan production (particularly the activity of promoting aggrecan production in articular chondrocytes)" as used herein is not particularly limited, but it can be confirmed by, for example, the following method (preferably a method described in Example 16). In this method, appropriate cells (particularly human articular chondrocytes) are respectively infected with a virus obtained by transfection with a virus vector comprising a polynucleotide encoding the polypeptide or a control virus obtained by transfection with a control virus vector not comprising the polynucleotide. After a predetermined number of days, such as 4 or 7 days, from the infection, an amount of aggrecan mRNA expressed in each cell is measured. When the amount of aggrecan mRNA expressed increases in the cells infected with the virus obtained by transfection with a virus vector comprising a polynucleotide encoding the polypeptide, in comparison with that infected with the control virus, it can be decided that the polypeptide exhibits the "activity of promoting aggrecan production (particularly the activity of promoting aggrecan production in articular chondrocytes)".

The variation functionally equivalent of the present invention is not particularly limited, so long as it is a polypeptide having an amino acid sequence in which one or plural (preferably 1 to 22, more preferably 1 to 10, most preferably 1 to 5) such as 1 or several amino acids are deleted, substituted, and/or added at one or plural positions in the amino acid sequence of the polypeptide 23/388, and exhibiting the activity of promoting type II collagen production (preferably the activity of promoting type II collagen production in articular chondrocytes) and/or the activity of promoting aggrecan production (preferably the activity of promoting aggrecan production in articular chondrocytes). A polypeptide exhibiting both the activity of promoting type II collagen production (preferably the activity of promoting type II collagen production in articular chondrocytes) and the activity of promoting aggrecan production (preferably the activity of promoting aggrecan production in articular chondrocytes) is preferable.

An origin of the variation functionally equivalent of the present invention is not limited to a human. The variation functionally equivalent of the present invention includes, for example, human variations of the polypeptide 23/388 and variations functionally equivalent derived from organisms other than a human (such as a mouse, a rat, a hamster, or a dog), and further polypeptides obtained by artificially modifying these native polypeptides (i.e., human variations or variations functionally equivalent derived from organisms other than a human) or the polypeptide 23/388 by genetic engineering techniques. The term "variation" as used herein means an individual difference between the same polypeptides in the same species or a difference between homologous polypeptides in several species.

Human variations of the polypeptide 23/388 or variations functionally equivalent derived from organisms other than a human can be obtained by those skilled in the art in accordance with the information of a sequence (for example, the base sequence consisting of the 103rd to 1203rd bases in the base sequence of SEQ ID NO: 1) of a gene encoding the polypeptide 23/388. In this connection, genetic engineering techniques can be generally performed in accordance with known methods (for example, a laboratory manual for genetic engineering techniques such as Sambrook, J. et al., "Molecular Cloning-A Laboratory Manual", Cold Spring Harbor Laboratory, NY, 1989).

For example, an appropriate probe or appropriate primers are designed in accordance with the information of a base sequence of a gene encoding the polypeptide 23/388. A polymerase chain reaction (PCR) method (Saiki, R. K. et al., Science, 239, 487–491, 1988) or a hybridization method is carried out using a sample (for example, total RNA or an mRNA fraction, a cDNA library, or a phage library) derived from an organism (for example, a mammal such as a human, a mouse, a rat, a hamster, or a dog) of interest and the primers or the probe to obtain a gene encoding the polypeptide. A desired polypeptide can be obtained by expressing the resulting gene in an appropriate expression system and confirming that the expressed polypeptide exhibits the activity of promoting type II collagen production in articular chondrocytes by, for example, the method described in Example 12 or the activity of promoting aggrecan production in articular chondrocytes by, for example, the method described in Example 16.

Further, the artificially modified polypeptide by genetic engineering techniques can be obtained by, for example, the following procedure. A gene encoding the polypeptide is obtained by a conventional method such as site-specific mutagenesis (Mark, D. F. et al., Proc. Natl. Acad. Sci. USA, 81, 5662–5666, 1984). A desired polypeptide can be obtained by expressing the resulting gene in an appropriate expression system and confirming that the expressed polypeptide exhibits the activity of promoting type II collagen production in articular chondrocytes by, for example, the method described in Example 12 or the activity of promoting aggrecan production in articular chondrocytes by, for example, the method described in Example 16.

The variation functionally equivalent of the present invention includes a polypeptide comprising the polypeptide 23/388 [or a polypeptide having an amino acid sequence in which one or plural (preferably 1 to 22, more preferably 1 to 10, most preferably 1 to 5) such as 1 or several amino acids are deleted, substituted, and/or added at one or plural positions in the amino acid sequence of the polypeptide 23/388 ], for example, a polypeptide (i.e., a fusion polypeptide) in which an appropriate marker sequence or the like is added to the N-terminus and/or the C-terminus thereof, so long as it exhibits the activity of promoting type II collagen production (preferably the activity of promoting type II collagen production in articular chondrocytes) and/or the activity of promoting aggrecan production (preferably the activity of promoting aggrecan production in articular chondrocytes).

As the marker sequence, a sequence for easily carrying out a confirmation of polypeptide expression, a confirmation of intracellular localization thereof, a purification thereof, or the like can be used. As the sequence, there may be mentioned, for example, a FLAG epitope, a hexa-histidine tag, a hemagglutinin tag, or a myc epitope.

The variation functionally equivalent of the present invention includes a polypeptide consisting of the amino acid sequence of SEQ ID NO: 2 (i.e., the amino acid sequence consisting of the 1 st to 388th amino acids in the amino acid sequence of SEQ ID NO: 2) per se, a polypeptide having an amino acid sequence in which one or plural (preferably 1 to 22, more preferably 1 to 10, most preferably 1 to 5) such as 1 or several amino acids are deleted, substituted, and/or added at one or plural positions in the amino acid sequence of SEQ ID NO: 2, or a polypeptide (i.e., a fusion polypeptide) in which an appropriate marker sequence or the like is added to the N-terminus and/or the C-terminus of these polypeptides, so long as it exhibits the activity of promoting type II collagen production (preferably the activity of promoting type II collagen production in articular chondrocytes) and/or the activity of promoting aggrecan production (preferably the activity of promoting aggrecan production in articular chondrocytes).

The homologous polypeptide of the present invention is not particularly limited, so long as it is a polypeptide having an amino acid sequence having a 90% or more homology with the amino acid sequence of the polypeptide 23/388 or the amino acid sequence of SEQ ID NO: 2 (i.e., the amino acid sequence consisting of the 1st to 388th amino acids in the amino acid sequence of SEQ ID NO: 2), and exhibiting the activity of promoting type II collagen production (preferably the activity of promoting type II collagen production in articular chondrocytes) and/or the activity of promoting aggrecan production (preferably the activity of promoting aggrecan production in articular chondrocytes). The homologous polypeptide of the present invention may have an amino acid sequence having preferably a 95% or more homology, more preferably a 98% or more homology, most preferably a 99% or more homology, with respect to the amino acid sequence of the polypeptide 23/388 or the amino acid sequence of SEQ ID NO: 2. Further, a polypeptide exhibiting both the activity of promoting type II collagen production (preferably the activity of promoting type II collagen production in articular chondrocytes) and the activity of promoting aggrecan production (preferably the activity of promoting aggrecan production in articular chondrocytes) is more preferable. The term "homology" as used herein means a value which can be obtained by a BLAST package [Basic local alignment search tool; Altschul, S. F. et al., J. Mol. Biol., 215, 403–410, (1990)]. The homology in the amino acid sequence can be calculated by a BLAST search algorithm. More particularly, this value can be obtained by using a bl2seq program (Tatiana A. Tatusova and Thomas L. Madden, FEMS Microbiol. Lett., 174, 247–250, 1999) with a default parameter in a BLAST package (sgi32 bit edition, version 2.0.12; obtained from NCBI). Default parameters of a bl2seq program include "blastp" as a search program, "0" as a cost to open a gap, "0" as a cost to extend a gap, "SEG" as a filter of the query sequence, and "BLOSUM62" as a matrix.

The polynucleotide of the present invention is not particularly limited, so long as it encodes the polypeptide of the present invention. As the polynucleotide of the present invention, there may be mentioned, for example, a polynucleotide having a base sequence consisting of the 103rd to 1203rd bases in the base sequence of SEQ ID NO: 1, or a polynucleotide having a base sequence consisting of the 37th to 1203rd bases in the base sequence of SEQ ID NO: 1. In addition, the term "polynucleotide" as used herein includes both DNA and RNA. The polynucleotide having a base sequence consisting of the 103rd to 1203rd bases in the base sequence of SEQ ID NO: 1 encodes the polypeptide 23/388. The polynucleotide having a base sequence consisting of the 37th to 1203rd bases in the base sequence of SEQ ID NO: 1 encodes the polypeptide consisting of the amino acid sequence of SEQ ID NO: 2.

The polynucleotide of the present invention can be used for not only producing the recombinant polypeptide of the present invention, but also producing the polypeptide of the present invention inside the body in gene therapy application.

A method for producing the polynucleotide of the present invention is not particularly limited, but there may be mentioned, for example, (1) a method using PCR, (2) a method using conventional genetic engineering techniques (i.e., a method for selecting a transformant comprising a desired cDNA from strains transformed with a cDNA library), or (3) a chemical synthesis method. These methods will be explained in this order hereinafter.

In the method using PCR, the polynucleotide of the present invention can be produced, for example, by the following procedure.

mRNA is extracted from human cells or tissue capable of producing the polypeptide of the present invention. Two primers which interpose full-length mRNA or a part of mRNA corresponding to the polypeptide of the present invention are synthesized on the basis of the base sequence of a polynucleotide encoding the polynucleotide of the present invention. Full-length cDNA encoding the polypeptide of the present invention or a part of the cDNA can be obtained by appropriately selecting conditions for a denaturing temperature or an addition of a denaturing agent and the like and by performing a reverse transcriptase-polymerase chain reaction (RT-PCR) appropriate to each of the synthesized primer pair.

Alternatively, full-length cDNA encoding the polypeptide of the present invention or a part of the cDNA can be obtained by performing PCR using, as a template, cDNA produced by reverse transcriptase from mRNA prepared from human cells or tissue-capable of producing the polypeptide of the present invention or commercially available cDNA derived from human cells or tissue.

More particularly, total RNA containing mRNA encoding the polypeptide of the present invention is extracted by a known method from cells or tissue capable of producing the polypeptide of the present invention. As an extraction method, there may be mentioned, for example, a guanidine thiocyanate-hot phenol method, a guanidine thiocyanate-guanidine hydrochloride method, or a guanidine thiocyanate-cesium chloride method. The guanidine thiocyanate-cesium chloride method is preferably used. The cells or tissue capable of producing the polypeptide of the present invention can be identified, for example, by a northern blotting method using a polynucleotide or a part thereof encoding the polypeptide of the present invention or a western blotting method using an antibody specific for the polypeptide of the present invention.

Next, the extracted mRNA is purified. Purification of the mRNA can be made in accordance with a conventional method, for example, the mRNA can be purified by the adsorption and elution using an oligo(dT)-cellulose column. The mRNA can be further fractionated by, for example, a sucrose density gradient centrifugation, if necessary. Alternatively, commercially available extracted and purified mRNA can be used, without carrying out the extraction of the mRNA.

Next, the first-strand cDNA is synthesized by carrying out a reverse transcriptase reaction of the purified mRNA in the presence of a random primer, an oligo dT primer, and/or a custom-synthesized primer. This synthesis can be carried out in accordance with a conventional method. The resulting first-strand cDNA is subjected to PCR using two primers which interpose a full-length or a partial region of the polynucleotide of interest, thereby amplifying the cDNA of interest. The resulting DNA is fractionated by, for example, an agarose gel electrophoresis. A DNA fragment of interest can be obtained by carrying out digestion of the DNA with restriction enzymes and subsequent ligation, if necessary.

In the method using conventional genetic engineering techniques, the polynucleotide of the present invention can be produced, for example, by the following procedure.

First, single-strand cDNA is synthesized using reverse transcriptase and using the mRNA prepared by the above-mentioned method as a template, and then double-strand cDNA is synthesized from the single-strand cDNA. As this method, there may be mentioned, for example, an S1 nuclease method (Efstratiadis, A. et al., Cell, 7, 279–288, 1976), a Land method (Land, H. et al., Nucleic Acids Res., 9, 2251–2266, 1981), an O. Joon Yoo method (Yoo, O. J. et al., Proc. Natl. Acad. Sci. USA, 79, 1049–1053, 1983), and an Okayama-Berg method (Okayama, H. and Berg, P., Mol. Cell. Biol., 2, 161–170, 1982).

Next, a recombinant plasmid comprising the double-strand cDNA is prepared and introduced into an *Escherichia coli* strain, such as DH 5a, HB101, or JM109, thereby transforming the strain. A transformant is selected using a drug resistance against, for example, tetracycline, ampicillin, kanamycin, or the like as a marker. When the host cell is *E. coli*, transformation of the host cell can be carried out, for example, by the method of Hanahan (Hanahan, D. J., Mol. Biol., 166, 557–580, 1983): namely, a method in which the recombinant DNA is added to competent cells prepared in the presence of $CaCl_2$, $MgCl_2$, or RbCl. Alternatively, a commercially available competent cell can be used. Further, as a vector other than a plasmid, a phage vector such as a lambda system can be used.

As a method for selecting a transformant containing the cDNA of interest from the resulting transformants, various methods such as (1) a screening method using a synthetic oligonucleotide probe, (2) a screening method using a probe produced by PCR, (3) a method in which screening is carried out by producing the polypeptide of interest in other animal cells, (4) a method in which the selection is carried out using an antibody against the polypeptide of the present invention, or (5) a method using a selective hybridization translation system, can be used.

In the screening method using a synthetic oligonucleotide probe, the transformant containing the cDNA of interest can be selected, for example, by the following procedure.

An oligonucleotide which corresponds to the whole or a part of the polypeptide of the present invention is synthesized (in this case, it can be either a nucleotide sequence taking the codon usage into consideration or a plurality of nucleotide sequences as a combination of possible nucleotide sequences, and in the latter case, their numbers can be reduced by including inosine) and, using this oligonucleotide as a probe (labeled with $^{32}P$ or $^{33}P$), hybridized with a nitrocellulose filter or a polyamide filter on which DNAs of the transformants are denatured and fixed, to screen and select resulting positive strains.

In the screening method using a probe produced by PCR, the transformant containing the cDNA of interest can be selected, for example, by the following procedure.

Oligonucleotides of a sense primer and an antisense primer corresponding to a part of the polypeptide of the present invention are synthesized, and a DNA fragment encoding the whole or a part of the polypeptide of interest is amplified by carrying out PCR using these primers in combination. As a template DNA used in this method, cDNA synthesized by a reverse transcription reaction from mRNA of cells capable of producing the polypeptide of the present invention, or genomic DNA can be used. The resulting DNA fragment is labeled with $^{32}P$ or $^{33}P$, and a transformant containing the cDNA of interest is selected by carrying out a colony hybridization or a plaque hybridization using this fragment as a probe.

In the method in which screening is carried out by producing the polypeptide of interest in other animal cells, the transformant containing the cDNA of interest can be selected, for example, by the following procedure.

The polynucleotides are amplified by culturing the transformants, and animal cells are transfected with the polynucleotides (in this case, either a plasmid which can self-replicate and contains a transcription promoter region or a plasmid which can be integrated into the chromosome of animal cells can be used), thereby producing the polypeptides encoded by the polynucleotides outside the cells. A transformant containing the cDNA of interest is selected from the original transformants by detecting the polypeptide of the present invention using an antibody against the polypeptide of the present invention.

In the method in which the selection is carried out using an antibody against the polypeptide of the present invention, the transformant containing the cDNA of interest can be selected, for example, by the following procedure.

First, cDNA is integrated into an expression vector, and polypeptides are produced into a culture supernatant, inside the cells, or on the cell surface of transformants. A transformant containing the cDNA of interest is selected by detecting a strain producing the desired polypeptide using an antibody against the polypeptide of the present invention and a second antibody against this antibody.

In the method using a selective hybridization translation system, the transformant containing the cDNA of interest can be selected, for example, by the following procedure.

First, cDNA obtained from each transformant is blotted on, for example, a nitrocellulose filter and hybridized with mRNA prepared from cells capable of producing the polypeptide of the present invention, and then the mRNA hybridized to the cDNA is dissociated and recovered. The recovered mRNA is translated into a polypeptide in an appropriate polypeptide translation system, for example, injection into *Xenopus* oocytes or a cell-free system such as a rabbit reticulocyte lysate, wheat germ or the like. A transformant containing the cDNA of interest is selected by detecting it with the use of an antibody against the polypeptide of the present invention.

A method for collecting the polynucleotide of the present invention from the resulting transformant of interest can be carried out in accordance with a known method (for example, a laboratory manual for genetic engineering techniques such as Sambrook, J. et al., "Molecular Cloning-A Laboratory Manual," Cold Spring Harbor Laboratory, NY, 1989). For example, it can be carried out by separating a fraction corresponding to the plasmid DNA from cells and cutting out the cDNA region from the plasmid DNA.

In the chemical synthesis method, the polynucleotide of the present invention can be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Further, the polynucleotide of the present invention can be produced by nucleic acid chemical synthesis in accordance with a conventional method such as a phosphite triester method (Hunkapiller, M. et al., Nature, 10, 105–111, 1984), based on the information on the polypeptide of the present invention. In this connection, codons for each amino acid are known and can be optionally selected and determined by the conventional method, for example, by taking a codon usage of each host to be used into consideration (Crantham, R. et al., Nucleic Acids Res., 9, r43-r74, 1981). Further, a partial modification of codons of these base sequences can be carried out in accordance with a conventional method, such as site specific mutagenesis which uses a primer comprised of a synthetic oligonucleotide coding for a desired modification (Mark, D. F. et al., Proc. Natl. Acad. Sci. USA, 81, 5662–5666, 1984).

Determination of the DNA sequences obtained by the above-mentioned methods can be carried out by, for example, a Maxam-Gilbert chemical modification method (Maxam, A. M. and Gilbert, W., "Methods in Enzymology", 65, 499–559, 1980) or a dideoxynucleotide chain termination method (Messing, J. and Vieira, J., Gene, 19, 269–276, 1982) and the like.

A eucaryotic or procaryotic host cell can be transformed by re-integrating an isolated polynucleotide of the present invention into an appropriate vector DNA and using the resulting expression vector. Further, it is possible to express the polynucleotide in a desired host cell, by introducing an appropriate promoter and a sequence related to the gene expression into the vector.

The expression vector of the present invention is not limited, so long as it comprises the polynucleotide of the present invention. As the expression vector, there may be mentioned, for example, an expression vector obtained by introducing the polynucleotide of the present invention into a known expression vector appropriately selected in accordance with a host cell to be used.

The cell of the present invention is not limited, so long as it is transfected with the expression vector of the present invention and comprises the polynucleotide of the present invention. A cell in which the polynucleotide is integrated into a chromosome of a host cell, or a cell containing the polynucleotide as an expression vector comprising the polynucleotide can be exemplified as the cell of the present invention. Further, the cell of the present invention can be a cell expressing the polypeptide of the present invention, or a cell not expressing the polypeptide of the present invention. The cell of the present invention can be obtained by, for example, transfecting a desired host cell with the expression vector of the present invention.

As the eucaryotic host cells, for example, cells of vertebrates, insects, yeast and the like are included. As the vertebral cell, there may be mentioned, for example, a COS cell as a simian cell (Gluzman, Y., Cell, 23, 175–182, 1981), a dihydrofolate reductase defective strain of a Chinese hamster ovary cell (CHO) (Urlaub, G. and Chasin, L. A., Proc. Natl. Acad. Sci. USA, 77, 4216–4220, 1980), a human embryonic kidney derived HEK293 cell, or a 293-EBNA cell (Invitrogen) obtained by introducing an EBNA-1 gene of Epstein Barr Virus into HEK293 cell.

The expression vector of the present invention includes an expression vector for producing the recombinant polypeptide of the present invention and an expression vector for producing the polypeptide of the present invention inside a body in gene therapy application.

As an expression vector for a vertebral cell, a vector containing a promoter positioned upstream of the polynucleotide to be expressed, an RNA splicing site, a polyadenylation site, a transcription termination sequence, and the like can be generally used. The vector can further contain a replication origin, if necessary. As the expression vector, there may be mentioned, for example, pSV2dhfr containing an SV40 early promoter (Subramani, S. et al., Mol. Cell. Biol., 1, 854–864, 1981), pEF-BOS containing a human elongation factor promoter (Mizushima, S. and Nagata, S., Nucleic Acids Res., 18,5322, 1990), or pCEP4 containing a cytomegalovirus promoter (Invitrogen), and the like.

When the COS cell is used as the host cell, a vector which has an SV40 replication origin, can perform an autonomous replication in the COS cell, and a vector which has a transcription promoter, a transcription termination signal, and an RNA splicing site, can be used as the expression vector. As the vector, there may be mentioned, for example, pME18S (Maruyama, K. and Takebe, Y., Med. Immunol., 20, 27–32, 1990), pEF-BOS (Mizushima, S. and Nagata, S., Nucleic Acids Res., 18, 5322, 1990), or pCDM8 (Seed, B., Nature, 329, 840–842, 1987).

The expression vector can be incorporated into COS cells by, for example, a DEAE-dextran method (Luthman, H. and Magnusson, G., Nucleic Acids Res., 11, 1295–1308, 1983), a calcium phosphate-DNA co-precipitation method (Graham, F. L. and van der Ed, A. J., Virology, 52, 456–457, 1973), a method using a commercially available transfection reagent (for example, FUGENE™ 6 Transfection Reagent; Roche Diagnostics), an electroporation method (Neumann, E. et al., EMBO J., 1, 841–845, 1982), or the like.

When the CHO cell is used as the host cell, a transformant cell capable of stably producing the polypeptide of the present invention can be obtained by carrying out co-transfection of an expression vector comprising the polynucleotide encoding the polypeptide of the present invention, together with a vector capable of expressing a neo gene which functions as a G418 resistance marker, such as pRSVneo (Sambrook, J. et al., "Molecular Cloning-A Laboratory Manual", Cold Spring Harbor Laboratory, NY, 1989) or pSV2-neo (Southern, P. J. and Berg, P., J. Mol. Appl. Genet., 1, 327–341,1982), and selecting a G418 resistant colony.

When the 293-EBNA cell is used as the host cell, for example, pCEP4 (Invitrogen) containing a replication origin of Epstein Barr Virus and being capable of performing an autonomous replication in the 293-EBNA cell can be used as the expression vector.

A vector for a gene therapy includes, for example, (1) a virus vector and (2) a non-virus vector. As the vector, a vector generally used (for example, a retrovirus vector, an adenovirus vector, Sendai virus vector, or the like as the virus vector) can be used [Takaku, F., Jikken Igaku (Supplement), "Frontier of gene therapy", Vol. 12, No. 15, 1994].

The cell of the present invention can be cultured in accordance with the conventional method, and the polypeptide of the present invention is produced outside the cells. As a medium to be used in the culturing, a medium commonly used in a desired host cell can be appropriately selected. In the case of the COS cell, for example, a medium such as an RPMI-1640 medium, a Dulbecco's modified Eagle's minimum essential medium (DMEM), or the like can be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 can be used.

The polypeptide of the present invention produced outside the cell of the present invention by culturing the cells can be separated and purified therefrom by various known separation techniques making use of the physical properties, biochemical properties and the like of the polypeptide. More particularly, the polypeptide of the present invention can be purified by treating a culture medium containing the polypeptide of the present invention with a commonly used treatment, for example, a treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), dialysis, or the like, or a combination thereof.

When the polypeptide of the present invention is expressed as a fusion protein with a marker sequence in frame, identification of the expression of the polypeptide of the present invention, purification thereof, or the like can be easily carried out. As the marker sequence, there may be mentioned, for example, a FLAG® epitope tag, a hexa-histidine tag, a hemagglutinin tag, or a myc epitope. Further, by inserting a specific amino acid sequence recognized by a protease such as enterokinase, factor Xa, or thrombin between the marker sequence and the polypeptide of the present invention, the marker sequence can be removed by the protease. For example, there is a report in which a muscarinic acetylcholine receptor and a hexa-histidine tag were connected by a thrombin recognition sequence (Hayashi, M. K. and Haga, T., J. Biochem., 120, 1232–1238, 1996).

Among the polypeptides of the present invention, the polypeptide capable of increasing an amount of type II collagen expression in articular chondrocytes is useful as an active ingredient of a pharmaceutical composition for promoting type II collagen production in articular chondrocytes. Further, it is known that type II collagen plays an important role in carrying out a function as articular cartilage, and thus the polypeptide is useful as an active ingredient of a pharmaceutical composition for treating and/or preventing osteoarthritis.

Among the polypeptides of the present invention, the polypeptide capable of promoting aggrecan production is useful as an active ingredient of a pharmaceutical composition for promoting aggrecan production. Further, aggrecan is a major proteoglycan which forms a cartilaginous tissue, and thus the polypeptide is useful as an active ingredient of a pharmaceutical composition for treating and/or preventing osteoarthritis.

In the present invention, the polypeptide of the present invention can be administered alone, or optionally, together with a conventional carrier which is pharmaceutically, or as a veterinary treatment, acceptable to an animal, preferably a mammal (particularly a human).

Further, the polypeptide of the present invention can be used in the manufacture of a pharmaceutical composition for promoting type II collagen production, a pharmaceutical composition for promoting aggrecan production, or a pharmaceutical composition for treating and/or preventing osteoarthritis.

The pharmaceutical composition for promoting type II collagen production, the pharmaceutical composition for promoting aggrecan production, or the pharmaceutical composition for treating and/or preventing osteoarthritis of the present invention can be prepared using additives generally used in the preparation of medicaments, in according with the active ingredient.

Examples of administration include oral administration by tablets, pills, capsules, granules, fine granules, powders, oral solutions and the like, and parenteral administration by injections (e.g., intravenous, intramuscular, intraarticular administration or the like), suppositories, transdermal preparations, transmucosal absorption preparations and the like. Particularly, in the case of polypeptides which are digested by enzymes, a parenteral administration such as intravenous injection or the like, or administration using formulations in which the polypeptide is delivered without digestion to a lower gastrointestinal tract (such as jejunum, ileum, colon, or large intestine) where digestive enzymes are not very effective, is desirable. As these preparation techniques, there may be mentioned, for example, a sustained release preparation (for example, International Publication Pamphlet WO94/06414), a colon-specific drug release system (for example, International Publication Pamphlet WO95/28963), or a long-acting preparation (International Publication Pamphlet WO93/05771).

The injections for parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil or the like), alcohols (e.g., ethanol or the like), polysorbate 80 and the like.

The injections can further contain other additives such as solubilization assisting agents, preservatives, stabilizing agents, emulsifying agents, soothing agents, isotonicities, buffers, fillers, coloring agents, or thickening agents. As the solubilization assisting agents, for example, cyclodextrins or the like can be used. As the preservatives, for example, methyl p-benzoate or the like can be used. As the emulsifying agents, for example, lecithin or the like can be used. As the soothing agents, for example, benzyl alcohol or the like can be used. As the isotonicities, for example, sodium chloride or the like can be used. As the fillers, for example, maltose or the like can be used. As the thickening agents, for example, hyaluronic acid or the like can be used.

These injections are sterilized for example by filtration through a bacteria retaining filter, blending of a germicide or irradiation. Alternatively, they can be used by first making into sterile solid compositions and dissolving them in sterile water or other sterile solvent for injection use prior to their use.

The dose is optionally decided by taking into consideration for example symptoms, age, sex and the like of each patient to be administered.

For example, in the case of oral administration, the usual dosage for an adult (60 kg in weight) is about 0.01 to 1000 mg, preferably 0.01 to 100 mg per day. In the case of parenteral administration, the usual dosage is about 0.01 to 1000 mg, preferably 0.01 to 100 mg per day in the form of an injection.

As a method for transferring a gene for a gene therapy, for example, (1) a virus vector, (2) non-virus vector, or (3) a naked DNA can be used. As a gene therapy method, for example, a method for implanting gene-introduced cells into a subject (an ex vivo method), or a method for injecting these genes per se directly into a subject, not via cells, (an in vivo method) can be used [Niitsu, Y. et al, Tanpakushitsu Kakusan Koso (Supplement), "Gene therapy", Vol. 40, No. 17, 1995].

The method of administration is not particularly limited, so long as the effective amount reaches the affected part. Examples of the administration include, for example, systemic administration (such as intravenous, intra-arterial, subcutaneous, intramuscular, oral administration, or the like), topical administration (such as intraarticular administration, pith cavity administration, or the like), mucosal administration (such as intranasal administration, intratracheal administration, intraoral administration, or the like), and intestinal administration (such as in suppository form or the like). Among these administrations, intraarticular administration is preferable [Baragi, V. M., Curr. Opin. Mol. Ther., 2(2), 216–220, 2000].

Further, a pharmaceutical composition for promoting type II collagen production, promoting aggrecan production, and/or treatment and/or prevention can be prepared by mixing the polynucleotide or the expression vector of the present invention with a pharmaceutical acceptable carrier or solvent (such as a physiological saline, a pH buffer, a stabilizing agent, a preservative, a suspension, or the like). To improve the effect of the gene therapy, for example, a technique in which the vector per se is embedded in a biodegradable gel can be used. More particularly, a method (T. OCHIYA et al., Nature Medicine, 5, 707–710, 1999) for maintaining a DNA release using atelocollagen (KOKEN Tokyo, Japan) can be used. Further, to improve the efficiency of the introduction of the gene into cells, phospholipids and/or cholesterol can be contained.

An antibody, such as a polyclonal antibody or a monoclonal antibody, which reacts with the polypeptide of the present invention can be obtained by directly administering the polypeptide of the present invention or a fragment thereof to various animals. Alternatively, it can be obtained by a DNA vaccine method (Raz, E. et al., Proc. Natl. Acad. Sci. USA, 91, 9519–9523, 1994; or Donnelly, J. J. et al., J. Infect. Dis., 173, 314–320, 1996), using a plasmid into which a polynucleotide encoding the polypeptide of the present invention is inserted.

The polyclonal antibody can be produced from a serum or eggs of an animal such as a rabbit, a rat, a goat, a chicken, or the like, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody can be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody can be easily produced by those skilled in the art, according to, for example, a cell fusion method of Kohler and Milstein (Kohler, G. and Milstein, C., Nature, 256, 495–497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) can be used. As a fusing agent, polyethylene glycol can be used. As a medium for preparation of hybridomas, for example, a commonly used medium such as an Eagle's minimum essential medium, a Dulbecco's modified minimum essential medium, or an RPMI-1640 medium can be used by adding properly 10 to 30% of a fetal bovine serum. The fused strains can be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which can be purified are produced by culturing the resulting hybridomas in a medium for 2 to 4 days, or in the peritoneal cavity of a pristane-pretreated BALB/c strain mouse for 10 to 20 days. The resulting monoclonal antibodies in the culture supernatant or the ascites can be separated and purified by conventional polypeptide isolation and purification methods.

Antibody fragments comprising an active part of the antibody such as F(ab')$_2$, Fab, Fab', or Fv can be obtained by a conventional method, for example, by digesting the separated and purified antibodies with a protease such as pepsin or papain, and separating and purifying the resulting fragment by standard polypeptide isolation and purification methods.

Further, an antibody which reacts to the polypeptide of the present invention can be obtained in a form of single chain Fv or Fab in accordance with a method of Clackson et al. or a method of Zebedee et al. (Clackson, T. et al., Nature, 352, 624–628, 1991; or Zebedee, S. et al., Proc. Natl. Acad. Sci. USA, 89, 3175–3179, 1992). Furthermore, a humanized antibody can be obtained by immunizing a transgenic mouse in which mouse antibody genes are substituted with human antibody genes (Lonberg, N. et al., Nature, 368, 856–859, 1994).

EXAMPLES

The present invention now will be further illustrated by, but is by no means limited to, the following Examples. The procedures were performed in accordance with the known methods, for example, the methods disclosed in Sambrook, J., et al. ("Molecular Cloning—A Laboratory Manual", Cold Spring Harbor Laboratory, NY, 1989), or the like, unless otherwise specified.

Example 1

Determination of Full-Length ORF Gene Sequence of Polypeptide Consisting of Amino Acid Sequence of SEQ ID NO: 2

Commercially available cDNA libraries and primers designed by the present inventors were used to carry out a 5'-RACE (Rapid Amplification of cDNA Ends) and a 3'-RACE. The first step of PCR was carried out using commercially available human ovary and human uterus libraries (MARATHON®-Ready cDNA; manufactured by Clontech) as templates, a GSP2 primer represented by SEQ ID NO: 3 and an AP1 primer [attached to MARATHON®-Ready cDNA kit (Clontech)] as primers, and a Taq polymerase (LA-TAQ™; Takara-shuzo) as a DNA polymerase. PCR was carried out under conditions of 94° C. for 2 minutes, 5 repetitions of a cycle of 98° C. for 5 seconds and 72° C. for 90 seconds, 5 repetitions of a cycle of 98° C. for 5 seconds and 70° C. for 90 seconds, 25 repetitions of a cycle of 98° C. for 5 seconds and 68° C. for 90 seconds and a subsequent cycle of 68° C. for 5 minutes. Subsequently, a reaction product obtained from the primary PCR was used as a template to conduct a second nested PCR. The second PCR was carried out using the reaction product of the primary PCR as templates, a GSP1 primer represented by SEQ ID NO: 4 and an AP2 primer (attached to MARATHON®-Ready cDNA kit (Clontech)) as primers, and a Taq polymerase (LA-TAQ™; Takara-shuzo) as a DNA polymerase. PCR was carried out under conditions of 94° C. for 2 minutes, 5 repetitions of a cycle of 98° C. for 5 seconds and 72° C. for 90 seconds, 5 repetitions of a cycle of 98° C. for 5 seconds and 70° C. for 90 seconds, 20 repetitions of a cycle of 98° C. for 5 seconds and 68° C. for 90 seconds and a subsequent cycle of 68° C. for 5 minutes. A resulting product of the second PCR was electrophoresed, and a band was cut and purified by a DNA extracting kit (QIAQUICK® gel extraction kit; manufactured by QIAGEN). A resulting DNA fragment was used as a template together with the above GSP1 primer and a sequencing kit (Dye Terminator Cycle Sequencing Kit; Applied Biosystems, Perkin-Elmer)

to perform a DNA extension reaction. Thereafter, a base sequence was elucidated by an automated laser fluorescence sequencer (DNA sequencer PRISM® 377; Applied Biosystems, Perkin-Elmer) to determine a $1^{st}$ to $584^{th}$ base sequence of SEQ ID NO: 1.

A 3'-RACE was carried out to obtain a DNA fragment by repeating the procedures of the above 5'-RACE except that an F2 primer represented by SEQ ID NO: 5 and the AP1 primer were used as primers for the first step of PCR, and an F1 primer represented by SEQ ID NO: 6 and the AP2 primer were used as primers for the second PCR.

A base sequence was elucidated by repeating the procedures of the 5'-RACE except that the DNA fragment obtained by the 3'-RACE was used as the template together with the F1 primer to determine a 1033rd to 1702nd base sequence of SEQ ID NO: 1.

Thereafter, an open reading frame that encodes a polypeptide represented by SEQ ID NO: 2 was determined. More particularly, using a commercially available human ovary cDNA library (MARATHON®-Ready cDNA; Clontech) as a template, an NC5A primer represented by SEQ ID NO: 7 and the GSP1 primer as the primers, and a Pfu DNA polymerase (Native Pfu DNA polymerase; Stratagene) as the DNA polymerase, PCR was carried out under conditions of 94° C. for 2 minutes, 40 repetitions of a cycle of 94° C. for 30 seconds, 55° C. for 30 seconds and 74° C. for 2 minutes and at a subsequent cycle of 74° C. for 5 minutes. A resulting PCR product was subcloned in a cloning vector (PZERO®-2; manufactured by Invitrogen), using a ligation kit (DNA Ligation Kit Ver. 2; manufactured by Takara-shuzo), and a sequence was elucidated by an automated laser fluorescence sequencer.

Further, the procedures of the above PCR and those of the determination of the sequence of the PCR product were repeated except that a combination of an F3 primer represented by SEQ ID NO: 8 and a 155N3 primer represented by SEQ ID NO: 9 were used instead of the combination of the NC5A primer and the GSP1 primer.

As a result, it was revealed that the full-length ORF composed of the 37th to 1203rd sequence represented by SEQ ID NO: 1 encoded a novel polypeptide composed of 388 amino acids as shown in SEQ ID NO: 1. Further, it was revealed that the molecule has a domain structure in the order of a secretory signal sequence, a coiled-coil domain, and a fibrinogen-like domain, from the N-terminus to the C-terminus. The novel molecule has the domain structure similar to those of the angiopoietin family (Davis S. et al., Curr. Top. Microbiol. Immunol., 237, 173–185, 1999) and pT49 of the fibrinogen-like factor (Ruegg C. et al., Gene, 160, 257–262, 1995). A homology of the amino acid sequences was analyzed by a commercially available sequence homology analyzing program MEGALIGN® manufactured by DNASTAR to find angiopoietin-1 and pT49 as most similar genes but the homology of the amino acid sequence with the polypeptide represented by SEQ ID NO: 1 were only 21% and 22% respectively.

WO01/05825 published after the priority date of the present application discloses a base sequence (CG144) encoding a polypeptide having an amino acid sequence wherein one amino acid is different from the amino acid sequence of SEQ ID NO: 2, and an amino acid sequence deduced therefrom. WO01/05825 discloses that the polypeptide encoded by CG144 is an angiopoietin, but does not disclose an experimental support therefore, and further, does not disclose the activities exhibited by the polypeptide of the present invention, that is, the activity of promoting type II collagen production or the activity of promoting aggrecan production.

Example 2

Preparation of Expression Vector Having a FLAGS Epitope Tag Added to C-Terminus

A vector pCEP4 manufactured by Invitrogen was digested with restriction enzymes, ClaI and NsiI, and the termini were blunted. Then, the digested and blunted product was ligated to obtain an expression vector pCEP4d wherein an EBNA1 expression unit was removed. The resulting vector was digested with restriction enzymes, NheI and BamHI, and the resulting product was extracted with agarose gel to obtain a DNA fragment having about 7.7 kbp. A double strand of oligonucleotide prepared by annealing an oligonucleotide consisting of SEQ ID NO: 10 and an oligonucleotide consisting of SEQ ID NO: 11 was inserted into the resulting DNA fragment. A sequence of a resulting plasmid was analyzed to confirm that the desired sequence was included, and it was named plasmid pCEP4d-FLAG.

Using the vector pCEP4d-FLAG as a template, an oligonucleotide represented by SEQ ID NO: 12 and an oligonucleotide represented by SEQ ID NO: 13 as primers, and a DNA polymnerase (PYROBEST™ DNA polymerase; Takara-shuzo, PCR was carried out under a condition of 94° C. for 2 minutes, 40 repetitions of a cycle of 94° C. for 30 seconds, 55° C. for 30 seconds and 74° C. for 1 minutes and subsequent 74° C. for 5 minutes. A resulting DNA fragment having about 0.4 kbp was digested with a restriction enzyme, SpeI, and inserted into a vector pCEP4d-FLAG (about 7.7 kbp) which had been digested with XbaI. From the resulting clones, a desired clone having cloning sites and a tag, i.e., in the order of recognition sequence of XbaI, NheI, NotI, and BamHI, and the FLAG® epitope tag from the promoter to the downstream thereof was selected and named a vector pCEP4dE2-FLAG.

Example 3

Preparation of Plasmid Expressing Polypeptide Having a FLAG® Epitope Tag Added to C-Terminus The polypeptide consisting of the amino acid sequence of SEQ ID NO: 2 is secreted and expressed by cleaving the secretory signal sequence at the N-terminus. A plasmid for expressing the polypeptide having a FLAG® epitope tag added to a C-terminus of the above secreted and expressed polypeptide of the present invention, was prepared according to the following procedures.

First, a polynucleotide consisting of the 37th to the 1200th base sequence of SEQ ID NO: 1 was prepared by a PCR. More particularly, using the NC5A primer represented by SEQ ID NO: 7 and the GSP1 primer represented by SEQ ID NO: 4 as the primers, a commercially available human ovary cDNA library (MARATHON-READY™ cDNA; manufactured by Clontech) as a template, and the Pfu DNA polymerase (Native Pfu DNA polymerase; Stratagene) as the DNA polymerase, PCR was carried out under a condition of 94° C. for 2 minutes, 40 repetitions of a cycle of 94° C. for 30 seconds, 55° C. for 30 seconds and 74° C. for 2 minutes and subsequent 74° C. for 5 minutes. A resulting PCR product was purified by a DNA extraction kit (QIAQUICK® gel extraction kit; manufactured by QIAGEN).

Further, the procedures of the above PCR, and those of the purification of the PCR product obtained by said PCR, were repeated except that a combination of the F3 primer represented by SEQ ID NO: 8 and the 155N3 primer represented by SEQ ID NO: 9 was used instead of the combination of the NC5A primer and the GSP1 primer.

A PCR was carried out, using two purified PCR products, i.e., the PCR product prepared from the combination of the NC5A primer and the GSP1 primer, and the PCR product prepared from the combination of the F3 primer and the 155N3 primer, as templates, the NC5A primer and the 155N3 primer as primers, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. A resulting PCR product was purified by a DNA extraction kit (QIAQUICK® gel extraction kit; manufactured by QIAGEN).

Subsequently, a PCR was carried out, using purified PCR product as a template, a K5A primer represented by SEQ ID NO: 14 and the 155N3 primer as primers, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, a KpnI recognition sequence and a Kozak sequence were added to the 5'-terminus, and a NotI recognition sequence was added to the 3'-terminus.

The DNA fragment was subcloned into a cloning vector (PZERO™-2; manufactured by Invitrogen), and the sequence thereof was confirmed. Then, the DNA fragment was digested with restriction enzymes, KpnI and NotI, and inserted into the Kpn and NotI site of the pCEP4dE2-FLAG prepared in Example 2. A resulting plasmid was named pCEP-CDF-FLAG.

Further, a PCR was carried out, using a 155XB5 primer represented by SEQ ID NO: 15 and the 155X3 primer represented by SEQ ID NO: 16 as primers, the plasmid pCEP-CDF-FLAG as a template, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, an XbaI recognition sequence and a Kozak sequence were added to the 5'-terminus, and an XbaI recognition sequence was added to the 3'-terminus. The resulting DNA fragment was subcloned into a cloning vector (PZERO™-2; manufactured by Invitrogen) and the sequence was confirmed. Then, the DNA fragment was digested with a restriction enzyme, XbaI, and inserted into an XbaI site of a plasmid pEF-BOS (Mizushima, S. and Nagata, S., Nucleic Acids Res., 18, 5322, 1999). A resulting plasmid was named pBOS-CDF-FLAG.

Example 4

Preparation of Expression Vector Having Signal Sequence and a FLAG® Epitope Tag Added to N-Terminus A vector pCEP4 manufactured by Invitrogen was digested with restriction enzymes, ClaI and NsiI, and the termini were blunted. Then, the digested and blunted product was ligated to obtain an expression vector pCEP4d wherein an EBNA1 expression unit was removed. The resulting vector was digested with restriction enzymes, HindIII and XhoI, and the resulting product was extracted with agarose gel to obtain a DNA fragment having about 7.7 kbp. A double strand oligonucleotide prepared by annealing an oligonucleotide consisting of SEQ ID NO: 17 and an oligonucleotide consisting of SEQ ID NO: 18 was inserted into the resulting DNA fragment. A clone having the desired sequence was selected, and named plasmid pCEP4d-SignalFLAG.

Example 5

Preparation of Plasmid Expressing Ipolyyieptide Having a FLAG® Epitolpe Tag Added to N-Terminus A plasmid for expressing the polypeptide according to the present invention wherein a foreign signal peptide and a FLAG® epitope tag were added to the N-terminus of the polypeptide that has a 23rd to 388th amino acid sequence of SEQ ID NO:2, and that was absent from the signal peptide, i.e., an amino acid sequence of the polypeptide 23/388, was prepared according to the following procedures. The polypeptide according to the present invention is secreted and expressed by cleaving the secretory signal sequence at the N-terminus.

First, a polynucleotide consisting of the 103rd to 1203rd base sequence of SEQ ID NO: 1 was prepared by a PCR. More particularly, the PCR was carried out, using a 155SFB primer represented by SEQ ID NO: 19 and a 155TX primer represented by SEQ ID NO: 20 as primers, the plasmid prepared in Example 3 as a template, and the Pfu DNA polymerase (Native Pfu DNA polymerase; manufactured by Stratagene) as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, a BclI recognition sequence was added to the 5'-terminus, and an XhoI recognition sequence was added to the 3'-terminus. The resulting DNA fragment was subcloned into a cloning vector (PZER™-2; manufactured by Invitrogen) and the sequence was confirmed. Then, the DNA fragment was digested with restriction enzymes, BclI and XhoI, and inserted into a BamHI and XhoI site of a plasmid pCEP4d-SignalFLAG. A resulting plasmid was named pCEP-SF-CDF.

Further, a PCR was carried out, using a XbaSF primer represented by SEQ ID NO: 21 and a 155TerX primer represented by SEQ ID NO: 22 as primers, the plasmid pCEP-SF-CDF as a template, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, an XbaI recognition sequence was added to each of the 5'-terminus and the 3'-terminus, respectively. The resulting DNA fragment was subcloned into a cloning vector (PZERO™-2; manufactured by Invitrogen) and the sequence was confirmed. Then, the DNA fragment was digested with a restriction enzyme, XbaI, and inserted into a XbaI site of a pEF-BOS (Mizushima, S. and Nagata, S., Nucleic Acids Res., 18, 5322, 1999). A resulting plasmid was named pBOSSFCDF.

Example 6

Preparation of Plasmid and Bacmid for Expressing Polypeptide Having a FLAG® Enitope Tag Added to C-Terminus The polypeptide consisting of an amino acid sequence of SEQ ID NO: 2 according to the present invention is secreted and expressed by cleaving the secretory signal sequence at the N-terminus. A plasmid and a bacmid for expressing the polypeptide according to the present invention wherein a FLAGS epitope tag was added to the C-terminus of the polypeptide from which the signal peptide was deleted, were prepared according to the following procedures.

First, a PCR was carried out, using a 155XB primer represented by SEQ ID NO: 15 and a 155X3 primer represented by SEQ ID NO: 16 as primers, the plasmid pCEP-CDF-FLAG prepared in Example 3 as a template, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, a BclI recognition sequence and a Kozak sequence were added to the 5'-terminus, and an XbaI recognition sequence was added to the 3'-terminus. The resulting DNA fragment was subcloned into a cloning vector (PZEROm™-2; manufactured by Invitrogen) and the sequence was confirmed. Then, the DNA fragment was digested with restriction enzymes, BclI and XbaI, and inserted into a BamHI and XbaI site of a plasmid PFASTBAC™ 1 manufactured by LIFE TECHNOLOGIES. A resulting plasmid was named pFB-CDF-FLAG.

A recombinant bacmid DNA was prepared from the resulting plasmid which was named pFB-CDF-FLAG and a commercially available competent cell (DH10 BAC™ Competent Cells; manufactured by LIFE TECHNOLOGIES), in accordance with a protocol attached thereto. A resulting bacmid was named BAC-CDF-FLAG.

Example 7

Preparation of Plasmid and Bacmid Expressing Polypeptide Having a FLAG® Epitope Tag Added to N-Terminus A plasmid and a bacmid for expressing the polypeptide according to the present invention wherein a foreign signal peptide and a FLAG® epitope tag were added to the N-terminus of the polypeptide that has a 23rd to 388th amino acid sequence of SEQ ID NO: 2, and that was absent from the signal peptide, i.e., an amino acid sequence of the polypeptide 23/388, was prepared according to the following procedures. The polypeptide according to the present invention is secreted and expressed by cleaving the secretory signal sequence at the N-terminus.

First, a PCR was carried out, using an XbaSF primer represented by SEQ ID NO: 21 and a 155TerX primer represented by SEQ ID NO: 22 as primers, the plasmid pCEP-SF-CDF prepared in Example 5 as a template, and the Pfu DNA polymerase as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. In a resulting desired DNA fragment, an XbaI recognition sequence was added to each of the 5'-terminus and the 3'-terminus, respectively. The resulting DNA fragment was subcloned into a cloning vector (PZER™-2; manufactured by Invitrogen) and the sequence was confirmed. Then, the DNA fragment was digested with a restriction enzyme, XbaI, and inserted into an XbaI site of a plasmid PFASTBAC™ 1 manufactured by LIFE TECHNOLOGIES. A resulting plasmid was named pFB-SF-CDF.

A recombinant bacmid DNA was prepared from the resulting plasmid which was named pFB-SF-CDF and a commercially available competent cell (DH10BAC™ Competent Cells; manufactured by LIFE TECHNOLOGIES), in accordance with a protocol attached thereto. A resulting bacmid was named BAC-SF-CDF.

Example 8

Expression of Polyeeptide Having a FLAG® Epitolpe Tag Added to N-Terminus in Animal Cell Strain A commercially available transfection reagent (FUGENE™ 6 Transfection Reagent; manufactured by Roche Diagnostics) was used, in accordance with a protocol attached thereto, to introduce the expression plasmid pCEP-SF-CDF prepared in Example 5 into a 293-EBNA cell manufactured by Invitrogen. An existence of the desired polypeptide in a culture supernatant obtained 2 to 3 days after the introduction of the plasmid was confirmed by a western blotting using an antibody (mouse ANTI-FLAG® monoclonal antibody M2; manufactured by Sigma) against the FLAG® epitope tag added to the N-terminus.

More particularly, the culture supernatant was applied to an ANTI-FLAG® monoclonal antibody agarose affinity gel (ANTI-FLAG® M2 Monoclonal Antibody Agarose Affinity Gel; manufactured by Sigma), washed with a phosphate buffered saline (PBS), and eluted with 10 mmol/L Tris-HCl (pH 3.0). An eluted and purified polypeptide was electrophoresed on an SDS-containing acrylamide gel (SDS/4%–20% acrylamide gel; manufactured by Daiichi Pure Chemicals), and transferred to a polyvinylidene difluoride (PVDF) membrane by a blotting apparatus. To the resulting PVDF membrane, Block-ace (manufactured by Dainippon Pharmaceutical) was added to perform a blocking. Then, the products on the membrane were reacted successively with the mouse ANTI-FLAG® monoclonal antibody M2 and a rabbit anti-mouse IgG polyclonal antibody labeled with horseradish peroxidase (manufactured by Zymed or TAGO). Alternatively, after blocking, the products on the membrane were reacted successively with a biotinylated mouse ANTI-FLAG® monoclonal antibody M2 (manufactured by Sigma) and a streptoavidin labeled with horseradish peroxidase (manufactured by Amersham Pharmacia). After the reaction, an expression of the polypeptide was confirmed by a western blotting detecting system (ECL PLUS™ Western Blotting Detecting System; manufactured by Amersham Pharmacia).

A molecular weight of the expressed polypeptide was 55 kDa under the reducing condition on the SDS-polyacrylamide gel electrophoresis (SDS-PAGE), whereas a molecular weight of the expressed polypeptide was 130 kDa or more under the non-reducing condition on the SDS-PAGE. This means that the expressed polypeptide has a multimer structure.

Example 9

Expression of Polyjeptide Having a FLAG® Epitope Tag Added to C-Terminus in Insect Cell Strain A commercially available transfection reagent (CELLFECTIN® Reagent; manufactured by LIFE TECHNOLOGIES) was used, in accordance with a protocol attached thereto, to introduce the expression bacmid BAC-CDF-FLAG prepared in Example 6 into an Sf9 cell (manufactured by LIFE TECHNOLOGIES). An existence of the desired polypeptide in a culture supernatant obtained 2 to 3 days after the introduction of the bacmid was confirmed by an antibody against the FLAG® epitope tag added to the C-terminus.

More particularly, the culture supernatant was applied to an ANTI-FLAG® M2 monoclonal antibody agarose affinity gel (ANTI-FLAG® M2 Monoclonal Antibody Agarose Affinity Gel; manufactured by Sigma), washed with a phosphate buffered saline (PBS), and eluted with 10 mmol/L Tris-HCl (pH3.0). An eluted and purified polypeptide was electrophoresed on an SDS-containing acrylamide gel (SDS/ 4%–20% acrylamide gel; manufactured by Daiichi Pure Chemicals), and transferred to a PVDF membrane by a blotting apparatus. To the resulting PVDF membrane, Block-ace (manufactured by Dainippon Pharmaceutical) was added to perform a blocking. Then, the products on the membrane were reacted successively with the mouse ANTI-FLAG® monoclonal antibody M2 (manufactured by Sigma) and a rabbit anti-mouse IgG polyclonal antibody labeled with horseradish peroxidase (manufactured by Zymed or TAGO). Alternatively, after blocking, the products on the membrane were reacted successively with a biotinylated mouse ANTI-FLAG® monoclonal antibody M2 (manufactured by Sigma) and a streptoavidin labeled with horseradish peroxidase (manufactured by Ammersham Pharmacia). After the reaction, an expression of the polypeptide was confirmed by a western blotting detecting system (ECL PLUS™ Western Blotting Detecting System; manufactured by Ammersham Pharmacia).

A molecular weight of the expressed polypeptide was 50 kDa under the reducing condition on the SDS-PAGE, whereas a molecular weight of the expressed polypeptide was 100 kDa or more under the non-reducing condition on the SDS-PAGE. This means that the expressed polypeptide has a multimer structure.

Example 10

Analysis of Expression of mRNA Encoding Polypeptide Consisting of Amino Acid Sequence of SEQ ID NO: 2

(1) Preparation of template cDNA

An analysis of the expression of mRNA encoding the polypeptide consisting of the amino acid sequence of SEQ ID NO: 2 was carried out in accordance with a quantitative PCR. A commercially available cDNA panel [Human MTC™ Panel I, Human MTC™ Panel II, Human Immune System MTC™ Panel, Human Fetal MTC™ Panel, Human Cardiovascular MTC™ Panel, and Human Digestive System MTC™ Panel in Multiple Tissue cDNA (MTC™) Panel manufactured by Clontech] was used to analyze the expression in human tissues.

In an analysis of the expression in human knee articular cartilage tissue and human culture cells, a total RNA was prepared from the human knee articular cartilage tissues and human culture cells by a commercially available total RNA purifying reagent (ISOGEN®; manufactured by Nippon Gene). The resulting total RNA was reacted with DNase (manufactured by Nippon Gene) at 37° C. for 15 minutes. The resulting DNase-treated total RNA (0.5 µg) was converted to cDNA by a SUPERSCRIPT™ First Strand System (for RT-PCR; manufactured by LIFE TECHNOLOGIES).

(2) Quantitative determination of mRNA of polypeptide consisting of amino acid sequence of SEQ ID NO: 2 by quantitative PCR An expression of mRNA of the polypeptide consisting of the amino acid sequence of SEQ ID NO: 2 in human tissues and human culture cells was analyzed, using a sequence detector (PRISM®7700 Sequence Detection System; manufactured by Applied Biosystems) and cDNA prepared in Example 10(1) or a commercially available cDNA panel disclosed in Example 10(1) as a template. The F1 primer represented by SEQ ID NO: 6 and an oligonucleotide represented by SEQ ID NO: 23 were used as a primer pair. A PCR was carried out, using a commercially available PCR reagent (SYBR® Green PCR core reagent; manufactured by Applied Biosystems), under a condition of 95° C. for 10 minutes, 45 repetitions of a cycle of 94° C. for 15 seconds, 60° C. for 30 seconds and 72° C. for 1 minutes.

Further, a PCR was carried out, using human genomic DNA as a template and the primer pair as above under the same conditions to obtain a standard curve for calculating an amount of mRNA expressed. A PCR was carried out, using the cDNA as above and human genomic DNA as templates and an oligonucleotide represented by SEQ ID NO: 24 and an oligonucleotide represented by SEQ ID NO: 25 as the primer pair under the same conditions to calculate an amount of human glyceraldehyde-3-phosphate dehydrogenase (g3pdh) expressed, as an internal standard. An amount of the mRNA of the polypeptide consisting of the amino acid sequence of SEQ ID NO: 2 expressed in tissues and cells was shown as a ratio to an amount of mRNA of g3pdh expressed in tissues and cells to obtain an amount of the mRNA of the polypeptide consisting of the amino acid sequence of SEQ ID NO: 2 per specific amount of mRNA.

It was found that mRNA of the polypeptide consisting of the amino acid sequence of SEQ ID NO: 2 according to the present invention was expressed specifically in an articular cartilage and an ovary in human tissues. A commercially available cDNA panel was used to investigate an expression in human tissues other than an articular cartilage and an ovary, and found that the above mRNA was expressed little or nothing in 47 different tissues other than an articular cartilage and an ovary. For human culture cancer cell strains, the expression was found only in HCS-2/8, chondrosarcoma, whereas the expression was found little or nothing in 96 kinds of other human cancer cells. For human normal primary culture cell, the expression was found only in a human articular chondrocyte, whereas the expression was found little or nothing in 4 kinds of human endothelial cells and human mesenchymal stem cells.

Example 11

Expression Induction of mRNA of Polypeptide Consisting of Amino Acid Sequence of SEQ ID NO: 2, Accompanied by Differentiation to Chondrocyte (1) Induction of differentiation from mesenchymal stem cells to chondrocyte It is known that a human mesenchymal stem cell is differentiated to a chondrocyte when cultivated under the condition of spheroid pellet with a stimulation of TGF-β3 or the like (Pittenger M. F., et al., Science, 284, 143–147, 1999).

Normal human mesenchymal stem cells (manufactured by Bio Whittaker) were cultured in a human mesenchymal stem cells proliferation medium kit (manufactured by Bio Whittaker) to obtain $5 \times 10^5$ cells. Then, $2.5 \times 10^5$ cells were washed with an incomplete chondrogenesis induction medium [DMEM-high glucose (manufactured by LIFE TECHNOLOGIES), 1 mmol/L-sodium pyruvate (manufactured by LIFE TECHNOLOGIES), 0.35 mmol/L-proline (manufactured by LIFE TECHNOLOGIES), 0.1 µmol/L-dexamethasone (manufactured by Sigma), 0.17 mmol/L-ascorbic acid 2-phosphate (manufactured by Sigma), and ITS+1 Culture Supplement (manufactured by Sigma)], and suspended in 500 µL of a complete chondrogenesis induction medium [an incomplete cartilage differentiation induction medium containing 0.01 µg/mL TGF-β3 (manufactured by Sigma)]. Then, the cell suspension was centrifuged at 150×g for 5 minutes in a polypropylene tube to obtain a cell pellet. The resulting cell pellet was cultivated in an cell incubator as it was. The cell culture was continued for 2 weeks while the medium was changed to a complete chondrogenesis induction medium every 3 or 4 days, so that the cells were differentiated to chondrocytes.

(2) Expression induction of mRNA of polypeptide consisting of amino acid sequence of SEQ ID NO: 2

A total RNA was prepared from each of undifferentiated human mesenchymal stem cells and differentiated chondrocytes by a commercially available total RNA purifying reagent (ISOGEN®; manufactured by Nippon Gene). The resulting total RNA was reacted with DNase (manufactured by Nippon Gene) at 37° C. for 15 minutes. The resulting DNase-treated total RNA (0.5 µg) was converted to cDNA by a SUPERSCRIP™ First-Strand System (for RT-PCR; manufactured by LIFE TECHNOLOGIES).

An expression of mRNA of the polypeptide consisting of the amino acid sequence of SEQ ID NO: 2 in the undifferentiated human mesenchymal stem cells and differentiated chondrocytes was analyzed as in Example 10(2). To confirm that the mesenchymal stem cells differentiated to the chondrocytes, an expression of mRNAs of type II collagen and type IX collagen specifically expressed in a chondrocyte was determined. An amount of gene expression of type II collagen was measured as in Example 10(2), using an oligonucleotide represented by SEQ ID NO: 26 and an oligonucleotide represented by SEQ ID NO: 27 as a primer set. An amount of gene expression of type IX collagen was measured as in Example 10(2), using an oligonucleotide represented by SEQ ID NO: 28 and an oligonucleotide represented by SEQ ID NO: 29 as a primer set.

The results of measuring the expression of the gene encoding the polypeptide consisting of the amino acid sequence of SEQ ID NO: 2 according to the present invention before and after the differentiation of the human mesenchymal stem cells to the chondrocyte are shown in FIG. 1. In the mesenchymal stem cells before differentiated to the chondrocyte, little or no gene encoding type II collagen and type IX collagen were expressed, whereas the expression of the genes encoding type II collagen and type IX collagen was induced upon the differentiation to the chondrocytes. This shows that the mesenchymal stem cells were differentiated to the chondrocytes. As shown in FIG. 1, little or no mRNA of the polypeptide consisting of the amino acid sequence of SEQ ID NO: 2 according to the present invention was found in the mesenchymal stem cells before the differentiation, whereas an expression was remarkably induced as high as 40 times upon the differentiation to the chondrocytes.

(3) The time course of expression of mRNA of polypeptide consisting of amino acid sequence of SEQ ID NO: 2

Subsequently, an expression induction of the gene encoding the polypeptide according to the present invention was investigated in detail in the process of the differentiation of the human mesenchymal stem cells to the chondrocytes. The human mesenchymal stem cells were differentiated to the chondrocytes in accordance with the method disclosed in Example 11(1). A total RNA and cDNA were prepared from undifferentiated human mesenchymal stem cells, and cells cultivated for 2, 4, 8, 14, 17, 22, and 28 days after the differentiation induction, in accordance with the method disclosed in Example 11(2). An amount of the expressed gene encoding the polypeptide consisting of the amino acid sequence of SEQ ID NO: 2 according to the present invention in each cell was determined by the method disclosed in Example 10(2). As a result, the cultivation for 2, 4, 8, 14, 17, 22, and 28 days after the differentiation induction increased an amount of the expressed gene encoding the polypeptide consisting of the amino acid sequence of SEQ ID NO: 2 by 1, 2, 5, 4, 6, 12, and 16-fold in comparison with undifferentiated human mesenchymal stem cells. The above result shows that the induction of the expression of the gene encoding the polypeptide consisting of the amino acid sequence of SEQ ID NO: 2 is accompanied by the differentiation to a chondrocyte.

Example 12

Activity of Polypeintide Having a FLAG® Epitope Tag Added to C-Terminus on Induction of Differentiation to Chondrocytes Human articular chondrocytes (manufactured by BIO WHITTAKER) were cultured in a 6-wells plate containing a chondrocyte proliferation medium (manufactured by BIO WHITTAKER) to about 70% confluent. A transfection reagent (FUGENE™ 6 Transfection Reagent; manufactured by Roche Diagnostics) was used in accordance with a protocol attached thereto to introduce the expression plasmid pBOS-CDF-FLAG (2 µg) prepared in Example 3 or the plasmid pEF-BOS (2 µg) as a control into the human articular chondrocytes. A total RNA was prepared from cells cultured for 3 days in a chondrocyte differentiation medium (manufactured by BIO WHITTAKER) and converted to cDNA by the method disclosed in Example 10(1).

An amount of expressed mRNA of type II collagen was analyzed, using a sequence detector (PRISM®7700 Sequence Detection System; manufactured by Applied Biosystems) and the resulting cDNA as above as a template. An oligonucleotide represented by SEQ ID NO: 26 and an oligonucleotide represented by SEQ ID NO: 27 were used as a primer set. A PCR was carried out, using a PCR reagent (SYBR® Green PCR core reagent; manufactured by Applied Biosystems), under a condition of 95° C. for 10 minutes, 45 repetitions of a cycle of 94° C. for 15 seconds, 60° C. for 30 seconds and 72° C. for 1 minutes.

Further, a PCR was carried out, using the cDNA prepared from HCS-2/8, chondrosarcoma, as a template and the primer set as above under the same conditions to obtain a standard curve for calculating an amount of mRNA expressed. A PCR was carried out, using the cDNA as above and human genomic DNA as templates and the oligonucleotide represented by SEQ ID NO: 24 and the oligonucleotide represented by SEQ ID NO: 25 as the primer under the same conditions to calculate an amount of human g3pdh expressed, as an internal standard. An amount of the expressed mRNA of type II collagen in cells was shown as a ratio to an amount of expressed mRNA of g3pdh in cells to obtain an amount of the expressed mRNA of type II collagen per specific amount of mRNA.

An amount of type II collagen expressed was increased by about 2-fold in comparison with the case of transfection of pEF-BOS as a control plasmid, by transfecting the pBOS-CDF-FLAG which is the expression plasmid for the polypeptide having the FLAG® epitope tag sequence added to the C-terminus according to the present invention into the articular chondrocytes.

The above result clearly shows that an expression of the polypeptide of the present invention in a human articular chondrocyte increases an expression of type II collagen.

Example 13

Genomic Structure and Chromosome Mapping of Polynucleotide Encoding Polypeptide Consisting of the Amino Acid Sequence of SEQ ID NO: 2

Alignment between the sequence of SEQ ID NO: 1 and human genome draft sequence of accession NO. AC015500 generated by using a sequence homology analyzing program (MEGALIGN®; manufactured by DNASTAR) revealed the exon and intron structure of cDNA of the polypeptide consisting of the amino acid sequence of SEQ ID NO: 2. The result revealed that the polypeptide consisting of the amino acid sequence of SEQ ID NO: 2 was composed of eight exons, that is, exon 1 having a sequence consisting of 1 st to 132nd bases in the sequence of SEQ ID NO: 1, exon 2 having a sequence consisting of 133rd to 277th bases in the sequence of SEQ ID NO: 1, exon 3 having a sequence consisting of 278th to 381 st bases in the sequence of SEQ ID NO: 1, exon 4 having a sequence consisting of 382nd to 475th bases in the sequence of SEQ ID NO: 1, exon 5 having a sequence consisting of 476th to 576th bases in the sequence of SEQ ID NO: 1, exon 6 having a sequence consisting of 577th to 697th bases in the sequence of SEQ ID NO: 1, exon 7 having a sequence consisting of 698th to 883rd bases in the sequence of SEQ ID NO: 1, and exon 8 having a sequence consisting of 884th to 1702nd bases in the sequence of SEQ ID NO: 1.

The cDNA of the polypeptide consisting of the amino acid sequence of SEQ ID NO: 2 obtained in Example 1 was used in a BLAST® [Basic local alignment search tool; Altschul, S. F. et al., J. Mol. Biol., 215, 403–410, (1990)] search of the GENBANK®. A result shows that the cDNA of the polypeptide consisting of the amino acid sequence of SEQ ID NO: 2 is contained in BAC clones of accession No. AP002372 and accession No. AP000634. The BAC clones are composed of about 150 thousand base pairs and about 40 thousand base pairs, respectively, and mapped on the human chromosome 11q22. Therefore, it was found that the gene of the polypeptide consisting of the amino acid sequence of SEQ ID NO: 2 is mapped on the human chromosome 11q22. It was reported that Osteoarthritis-susceptibility locus is linked on the human chromosome 11q22 as a result of a genetic survey of lineages liable to suffer from OA or OA patients (Chapman K., et al., Am. J. Hum. Genet., 65, 167–174, 1999). Therefore, the possibility is presumed that a mutation of the gene of the polypeptide consisting of the amino acid sequence of SEQ ID NO: 2 causes a susceptibility of OA.

Example 14

Preparation of Adenovirus Vector for Expressing Polypeptide Having a FLAG® Epitope Tag Added to C-Terminus The polypeptide consisting of an amino acid sequence of SEQ ID NO: 2 is secreted and expressed by cleaving the secretory signal sequence at the N-terminus. A virus vector for expressing the polypeptide according to the present invention wherein a FLAG® epitope tag was added to the C-terminus of the secreted and expressed polypeptide was prepared according to the following procedures.

First, a PCR was carried out, using a 155 KB5 primer represented by SEQ ID NO: 30 and a 155Xh3 primer represented by SEQ ID NO: 31 as primers, the plasmid pCEP-CDF-FLAG prepared in Example 3 as a template, and the Pfu DNA polymerase (Native Pfu DNA polymerase; manufactured by Stratagene) as the DNA polymerase, under a condition of 94° C. for 2 minutes, 40 repetitions of a cycle of 94° C. for 30 seconds, 55° C. for 30 seconds and 74° C. for 2 minutes and subsequent 74° C. for 5 minutes. A resulting desired DNA fragment having a KpnI recognition sequence and a Kozak sequence added to the 5'-terminus, and an XhoI recognition sequence added to the 3'-terminus was subcloned into a cloning vector (PCR-Blunt; manufactured by Invitrogen) and the sequence was confirmed. Then, the DNA fragment was digested with restriction enzymes, KpnI and XhoI, and inserted into a KpnI and XhoI site of a plasmid pAdTrack-CMV (He T.-C., et al., Proc. Natl. Acad. Sci. USA, 95, 2509–2514, 1998). A resulting plasmid was named pAdTrack-CDF-Flag.

*E. coli* BJ5183 strain (manufactured by Stratagene) was transformed by a plasmid pAdEasy-1 (He T.-C., et al., Proc. Natl. Acad. Sci. USA, 95, 2509–2514, 1998) to obtain *E. coli* BJ5183 strain containing plasmid pAdEasy-1 [hereinafter referred to as *E. coli* BJ5183 (pAdEasy-1)]. The above plasmid pAdTrack-CDF-Flag was digested with a restriction enzyme, PmeI, and *E. coli* BJ5183 (pAdEasy-1) strain was transformed by a resulting digested plasmid. To select a clone wherein the plasmid pAdEasy-1 and the plasmid pAdTrack-CDF-Flag were recombinated, plasmids were prepared from the resulting transformed clones, and the fragment patterns of plasmid digested with a restriction enzyme, XhoI, were examined. In the case of plasmid pAdTrack-CDF-Flag, a clone having an extra band of 4.5 kb was selected. As a result, a clone having a designed recombination at an arm sites of the plasmid was obtained, and named virus vector pAd-CDF-Flag.

Further, the above procedures were repeated except that the plasmid pAdTrack-CMV, i.e., a negative control vector instead of the plasmid pAdTrack-CDF-Flag, was used to obtain virus vector pAd-CMV. In the case of the plasmid pAdTrack-CMV, a clone having an extra band of 3 kb was selected.

Example 15

Preparation and Purification of Virus

The virus vector pAd-CDF-Flag was digested with a restriction enzyme, PacI, and a commercially available transfection reagent (LIPOFECTAMINE™ 2000; manufactured by LIFE TECHNOLOGIES) was used in accordance with a protocol attached thereto to introduce the digested vector into HEK293 cells (manufactured by Dainippon Pharmaceutical). Transfected cells were cultured for 8 days after transfection, and cells were harvested after confirming the production of viruses. The virus vector pAd-CDF-Flag contains a green fluorescent protein (GFP) expression unit, and therefore, the cell into which the plasmid is introduced can be easily recognized by a fluorescence microscope. The harvested cells were suspended in PBS, and freezing and thawing procedures were repeated several times. Thereafter, a centrifugation was performed and a supernatant was recovered to obtain a primary virus solution vAd-CDF-Flag. The resulting virus was added to HEK 293 cells, and the cells were cultured for 3 days. When about 50% of the cells were detached, the cells were harvested and freezing and thawing procedures were carried out to prepare a virus fraction and a secondary virus solution. The procedures of the virus infection, the cell harvesting, and the virus fraction preparation as above were further repeated twice to finally obtain a virus solution from the virus-infected HEK293 cells cultured in 10 flasks (bottom area=150 cm$^2$). The virus solution was further purified by a cesium chloride density-gradient method. The resulting purified virus solution was dialyzed against a buffer [10 mmol/L Tris-HCl (pH7.5), 1 mmol/L MgCl$_2$, 135 mmol/L NaCl]. Then, the absorbance at 260 nm ($A_{260}$) was measured, and a concentration of virus particles (unit=particles/mL) was calculated by the equation:

$$A_{260} \times 1.1 \times 10^{12}.$$

As a result, in the case of the virus vAd-CDF-Flag prepared by transfecting the virus vector pAd-CDF-Flag, virus particles of $1.2. \times 10^{11}$ particles/mL were obtained.

The above procedures were repeated except that the virus vector pAd-CMV was used instead of the virus vector pAd-CDF-Flag. In the case of the vAd-CMV prepared by transfecting the virus vector pAd-CMV, virus particles of $5.9. \times 10^{10}$ particles/mL were obtained.

Example 16

Activity of Polypeptide Having a FLAGS Epitope Tag Added to C-Terminus on Induction of Differentiation to Chondrocytes Human articular chondrocytes (manufactured by BIO WHITTAKER) were cultured in a 6-wells plate containing a chondrocyte proliferation medium (manufactured by BIO WHITTAKER) to about 70% confluent. The viruses prepared in Example 15 (the virus vAd-CDF-Flag, or the virus vAd-CMV for a negative control) were added in two doses of the particle concentrations, i.e., $3 \times 10^7$ particles/well or $1 \times 10^8$ particles/well for each virus. The whole was cultured for 4 or 7 days in a chondrocyte differentiation medium (manufactured by BIO WHITTAKER). Thereafter, the cells were harvested, and an RNA preparation kit (RNEASY®; manufactured by QIAGEN) and DNase I (DNaseI; manufactured by QIAGEN) were used in accordance with the protocols attached thereto to obtain DNase-treated total RNA. The resulting DNase-treated total RNA (0.5 μg) was converted to cDNA by a SUPERSCRIPT™ First-Strand System (for RT-PCR; manufactured by LIFE TECHNOLOGIES).

An amount of expressed gene encoding type II collagen was determined by measuring a fluorescent amount in real time, using a sequence detector (PRISM®7700 Sequence Detection System; manufactured by Applied Biosystems) and the resulting cDNA as above as a template. An oligonucleotide represented by SEQ ID NO: 32 and an oligonucleotide represented by SEQ ID NO: 33 were used as a primer pair. A PCR was carried out, using a PCR reagent (SYBR® Green PCR core reagent; manufactured by Applied Biosystems), under conditions of 95° C. for 10 minutes, 45 repetitions of a cycle of 94° C. for 15 seconds, 60° C. for 30 seconds, and 72° C. for 1 minute. Further, a PCR was carried out using the cDNA prepared from human mesenchymal stem cells which had been stimulated for differentiation to chondrocytes for 3 weeks as a template and a primer pair as above under the same conditions to obtain a standard curve for calculating an amount of mRNA expressed.

An amount of expressed gene encoding aggrecan was determined by measuring a fluorescent amount in real time, using a sequence detector (PRISM®7700 Sequence Detection System; manufactured by Applied Biosystems) and the resulting cDNA as above as a template. An oligonucleotide represented by SEQ ID NO: 34 as a forward primer, an oligonucleotide represented by SEQ ID NO: 35 as a reverse primer, and a fluorescence-labeled oligonucleotide represented by SEQ ID NO: 36 manufactured by Applied Biosystems as a TAQMAN® probe were used. A PCR was carried out, using a buffer adequate for PCR incorporating TAQMAN® probes (TAQMAN® Buffer; manufactured by Applied Biosystems), under conditions of 95° C. for 10 minutes, 45 repetitions of a cycle of 95° C. for 15 seconds, 60° C. for 60 seconds. Further, a PCR was carried out using the cDNA prepared from unstimulated human articular chondrocytes or human mesenchymal stem cells which had been stimulated for differentiation to chondrocytes for 3 weeks as a template and the primer pair as above under the same conditions to obtain a standard curve for calculating an amount of mRNA expressed.

A PCR was carried out, using the cDNA as above and human genomic DNA as templates and the oligonucleotide represented by SEQ ID NO: 24 and the oligonucleotide represented by SEQ ID NO: 25 as the primer pair under the same conditions to calculate an amount of human g3pdh expressed, as an internal standard. An amount of each of the expressed genes encoding type II collagen and aggrecan in cells was shown as a ratio to an amount of expressed mRNA of g3pdh in cells to obtain an amount of the expressed mRNA per specific amount of mRNA.

Figure 2:
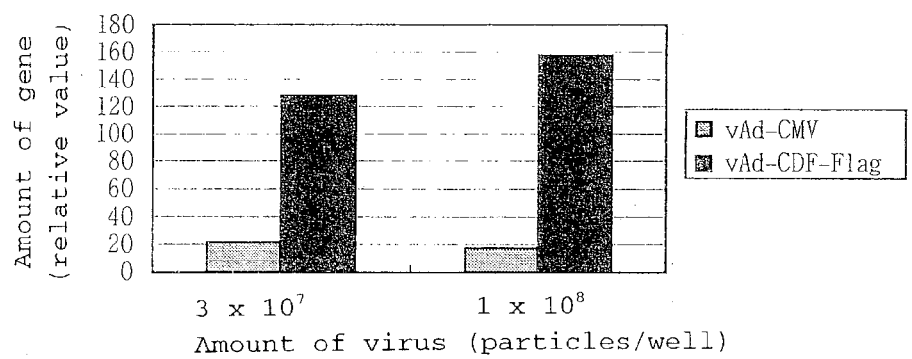
FIG. 2 is a graph showing an amount of type II collagen gene expressed 7 days after infection.
Figure 3:
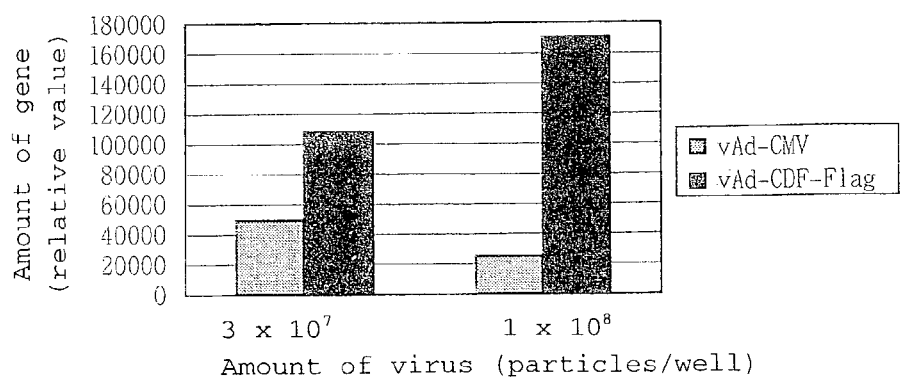
FIG. 3 is a graph showing an amount of aggrecan gene expressed 4 days after infection.

An amount of each of the expressed genes encoding type II collagen and aggrecan with respect to the days of cultivation and the concentration of infected viruses is shown in Table 1, as a relative amount with respect to an amount of each of expressed genes in the case of the infection with the virus vAd-CMV as a control. Among the results, an amount of the expressed gene encoding type II collagen at the 7th day after the infection is shown in FIG. 2, and an amount of the expressed gene encoding aggrecan at the 4th day after the infection is shown in FIG. 3.

A human articular chondrocyte spontaneously produces type II collagen and aggrecan. However, the amounts of the expressed genes encoding type II collagen and aggrecan were increased by exosinously expressing the polypeptide of the present invention in the cell, using the adenovirus vector, as shown in Table 1. As a negative control, a virus (vAd-CMV) not containing the cDNA coding polypeptide of the present invention was used.

When the virus vAd-CDF-Flag was added at the concentration of $3 \times 10^7$ particles/well or $1 \times 10^8$ particles/well, the amount of the type II collagen expressed was increased by about 2-fold after cultivating for 4 days, and by about 6-fold or about 9-fold respectively after the cultivating for 7 days, in the articular chondrocyte that expressed the polypeptide of the present invention by the infection of the virus vAd-CDF-Flag, in comparison with the case of the infection with the virus aAv-CMV. When the virus vAd-CDF-Flag was added at the concentration of $3 \times 10^7$ particles/well or $1 \times 10^8$ particles/well, the amount of the aggrecan expressed was increased by about 2-fold or about 7-fold after cultivating for 4 days, respectively, and by about 2-fold or about 3-fold after the cultivating for 7 days, respectively.

The results clearly show that the expression of type II collagen and aggrecan increased by expressing the polypeptide of the present invention in the human articular chondrocyte.

TABLE 1

| Days of cultivation Concentration of infected viruses | 4 days | | 7 days | |
|---|---|---|---|---|
| | $3 \times 10^7$ | $1 \times 10^8$ | $3 \times 10^7$ | $1 \times 10^8$ |
| Type II collagen | 1.7-fold | 2.2-fold | 5.9-fold | 9.1-fold |
| Aggrecan | 2.2-fold | 6.8-fold | 1.9-fold | 2.7-fold |

Industrial Applicability

Among the polypeptides of the present invention, the polypeptide having the activity of promoting type II collagen production is useful for an active ingredient of a pharmaceutical composition for promoting type II collagen production in articular chondrocytes, because type II collagen plays an important role for a function of articular cartilage. Further, type II collagen decreases in the OA disease, and thus the polypeptide is useful as an active ingredient of a pharmaceutical composition for treating and/or preventing osteoarthritis.

Among the polypeptides of the present invention, the polypeptide having the activity of promoting aggrecan production is useful as an active ingredient of a pharmaceutical composition for promoting aggrecan production, because aggrecan plays an important role for a function of articular cartilage. Further, aggrecan is a major proteoglycan which forms a cartilaginous tissue and is decomposed and degenerated in the OA disease, and thus the polypeptide is useful as an active ingredient of a pharmaceutical composition for treating and/or preventing osteoarthritis.

The polynucleotide, the expression vector, the cell, and the antibody of the present invention are useful for producing the polypeptide of the present invention.

Further, the polynucleotide and the expression vector of the present invention can be used for a gene therapy for promoting type II collagen production, promoting aggrecan production, and/or treating and/or preventing osteoarthritis.

Free Text in Sequence Listing

Features of "Artificial Sequence" are described in the numeric identifier <223> in the Sequence Listing. More particularly, each of the base sequences of SEQ ID NOS: 9, 12–16, 19–22, 30, and 31 is an artificially synthesized primer sequence. Each of the base sequences of SEQ ID NOS: 10, 11, 17, and 18 is an artificially synthesized linker sequence.

As above, the present invention is explained with reference to particular embodiments, but modifications and improvements obvious to those skilled in the art are included in the scope of the present invention.

The invention claimed is:

1. An isolated polynucleotide encoding a polypeptide selected from:
   (a) a polypeptide consisting of an amino acid sequence consisting of amino acids 23 to 388 of SEQ ID NO:2;
   (b) a polypeptide consisting of an amino acid sequence consisting of amino acids 1 to 388 of SEQ ID NO: 2;
   (c) a polypeptide comprising an amino acid sequence consisting of amino acids 23 to 388 of SEQ ID NO: 2, and exhibiting an activity of promoting type II collagen production and/or an activity of promoting aggrecan production; or
   (d) a polypeptide according to any one of (a), (b), or (c), exhibiting both an activity of promoting type II collagen production and an activity of promoting aggrecan production.

2. An expression vector comprising the polynucleotide according to claim 1.

3. An isolated cell transfected with the expression vector according to claim 2.

* * * * *